United States Patent
Zhou et al.

(10) Patent No.: US 9,907,520 B2
(45) Date of Patent: *Mar. 6, 2018

(54) DIGITAL TOMOSYNTHESIS SYSTEMS, METHODS, AND COMPUTER READABLE MEDIA FOR INTRAORAL DENTAL TOMOSYNTHESIS IMAGING

(71) Applicants: THE UNIVERSITY OF NORTH CAROLINA AT CHAPEL HILL, Chapel Hill, NC (US); Xintek, Inc., Research Triangle Park, NC (US)

(72) Inventors: Otto Z. Zhou, Chapel Hill, NC (US); Jianping Lu, Chapel Hill, NC (US); Jing Shan, Chapel Hill, NC (US); Andrew Tucker, Cary, NC (US); Pavel Chtcheprov, Chapel Hill, NC (US); Enrique Platin, Cary, NC (US); André Mol, Chapel Hill, NC (US); Laurence Rossman Gaalaas, Carrboro, NC (US); Gongting Wu, Chapel Hill, NC (US)

(73) Assignees: The University of North Carolina at Chapel Hill, Chapel Hill, NC (US); XINTEK, INC., Research Triangle Park, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/205,787

(22) Filed: Jul. 8, 2016

(65) Prior Publication Data

US 2016/0317107 A1    Nov. 3, 2016

Related U.S. Application Data

(63) Continuation of application No. 14/741,041, filed on Jun. 16, 2015.

(Continued)

(51) Int. Cl.
*A61B 6/14*    (2006.01)
*A61B 6/00*    (2006.01)
(Continued)

(52) U.S. Cl.
CPC .............. *A61B 6/145* (2013.01); *A61B 6/025* (2013.01); *A61B 6/06* (2013.01); *A61B 6/4007* (2013.01);
(Continued)

(58) Field of Classification Search
USPC .......................................... 378/22
See application file for complete search history.

(56) References Cited

U.S. PATENT DOCUMENTS

| 2,842,706 A | 7/1958 | Dobischek et al. |
| 3,617,285 A | 11/1971 | Staudenmayer |

(Continued)

FOREIGN PATENT DOCUMENTS

| CN | 101352353 | 1/2009 |
| CN | 101842052 | 9/2010 |

(Continued)

OTHER PUBLICATIONS

Brodie, et al., "Vacuum Microelectronics," Advance in Electronics and Electron Physics, edited by P.W. Hawkes, vol. 83, pp. 1-106 (1992).

(Continued)

*Primary Examiner* — Phillip A Johnston
(74) *Attorney, Agent, or Firm* — Jenkins, Wilson, Taylor & Hunt, P.A.

(57) ABSTRACT

Digital tomosynthesis systems, methods, and computer readable media for intraoral dental tomosynthesis imaging are disclosed. In some aspects, an intraoral tomosynthesis imaging system includes an x-ray source array for positioning outside a mouth of a patient, wherein the x-ray source (Continued)

array contains multiple x-ray focal spots that are spatially distributed on an anode, an area digital x-ray detector for positioning inside the mouth of the patient, a geometry calibration mechanism for connecting the x-ray detector to the x-ray source array, an x-ray collimator for confining x-ray beams to a region of interest, a controller for regulating x-ray radiation and synchronization of the x-ray radiation with the x-ray detector, such that multiple 2D projection images of the ROI are acquired without mechanical motion of the x-ray source array, the x-ray detector, or the mouth of the patient, and a computer program and workstation for 3D tomosynthesis image reconstruction and display.

8 Claims, 10 Drawing Sheets

Related U.S. Application Data

(60) Provisional application No. 62/143,443, filed on Apr. 6, 2015, provisional application No. 62/013,181, filed on Jun. 17, 2014.

(51) Int. Cl.
*A61B 6/02* (2006.01)
*A61B 6/06* (2006.01)

(52) U.S. Cl.
CPC ............ *A61B 6/4035* (2013.01); *A61B 6/425* (2013.01); *A61B 6/4405* (2013.01); *A61B 6/461* (2013.01); *A61B 6/5205* (2013.01); *A61B 6/5217* (2013.01); *A61B 6/547* (2013.01); *A61B 6/582* (2013.01); *A61B 6/587* (2013.01)

(56) References Cited

U.S. PATENT DOCUMENTS

| | | | |
|---|---|---|---|
| 3,733,484 A | 5/1973 | Bayard | |
| 3,753,020 A | 8/1973 | Zingaro | |
| 3,783,288 A | 1/1974 | Barbour et al. | |
| 3,921,022 A | 11/1975 | Levine | |
| 4,012,656 A | 3/1977 | Norman et al. | |
| 4,253,221 A | 3/1981 | Cochran, Jr. et al. | |
| 4,289,969 A | 9/1981 | Cooperstein et al. | |
| 4,958,365 A | 9/1990 | Sohval et al. | |
| 5,129,850 A | 7/1992 | Kane et al. | |
| 5,138,237 A | 8/1992 | Kane et al. | |
| 5,305,363 A | 4/1994 | Burke et al. | |
| 5,317,618 A | 5/1994 | Nakahara et al. | |
| 5,371,778 A | 12/1994 | Yanof et al. | |
| 5,377,249 A | 12/1994 | Wiesent et al. | |
| 5,424,054 A | 6/1995 | Bethune et al. | |
| 5,557,105 A | 9/1996 | Honjo et al. | |
| 5,578,821 A | 11/1996 | Meisberger et al. | |
| 5,616,368 A | 4/1997 | Jin et al. | |
| 5,623,180 A | 4/1997 | Jin et al. | |
| 5,637,950 A | 6/1997 | Jin et al. | |
| 5,648,699 A | 7/1997 | Jin et al. | |
| 5,726,524 A | 3/1998 | Debe | |
| 5,773,834 A | 6/1998 | Yamamoto et al. | |
| 5,773,921 A | 6/1998 | Keesmann et al. | |
| 5,786,895 A | 7/1998 | Mitchell et al. | |
| 5,828,722 A | 10/1998 | Ploetz et al. | |
| 5,834,783 A | 11/1998 | Muraki et al. | |
| 5,844,963 A | 12/1998 | Koller et al. | |
| 5,910,974 A | 6/1999 | Kuhn et al. | |
| 5,973,444 A | 10/1999 | Xu et al. | |
| 5,976,444 A | 11/1999 | Pearson et al. | |
| 6,019,656 A | 2/2000 | Park et al. | |
| 6,057,637 A | 5/2000 | Zettl et al. | |
| 6,087,765 A | 7/2000 | Coll et al. | |
| 6,250,984 B1 | 6/2001 | Jin et al. | |
| 6,259,765 B1 | 7/2001 | Baptist | |
| 6,271,923 B1 | 8/2001 | Hill | |
| 6,277,138 B1 | 8/2001 | Levinson et al. | |
| 6,280,697 B1 | 8/2001 | Zhou et al. | |
| 6,297,592 B1 | 10/2001 | Goren et al. | |
| 6,333,968 B1 | 12/2001 | Whitlock et al. | |
| 6,334,939 B1 | 1/2002 | Zhou et al. | |
| 6,385,292 B1 | 5/2002 | Dunham et al. | |
| 6,440,761 B1 | 8/2002 | Choi | |
| 6,445,122 B1 | 9/2002 | Chuang et al. | |
| 6,456,691 B2 | 9/2002 | Takahashi et al. | |
| 6,459,767 B1 | 10/2002 | Boyer et al. | |
| 6,470,068 B2 | 10/2002 | Cheng | |
| 6,498,349 B1 | 12/2002 | Thomas et al. | |
| 6,553,096 B1 | 4/2003 | Zhou et al. | |
| RE38,223 E | 8/2003 | Keesmann et al. | |
| 6,630,772 B1 | 10/2003 | Bower et al. | |
| 6,650,730 B2 | 11/2003 | Bogatu et al. | |
| 6,674,837 B1 | 1/2004 | Tasker et al. | |
| 6,753,931 B2 | 6/2004 | Kane et al. | |
| 6,760,407 B2 | 7/2004 | Price et al. | |
| RE38,561 E | 8/2004 | Keesmann et al. | |
| 6,850,595 B2 | 2/2005 | Zhou et al. | |
| 6,852,973 B2 | 2/2005 | Suzuki et al. | |
| 6,876,724 B2 | 4/2005 | Zhou et al. | |
| 6,965,199 B2 | 11/2005 | Stoner et al. | |
| 6,980,627 B2 | 12/2005 | Qiu et al. | |
| 7,082,182 B2 | 7/2006 | Zhou et al. | |
| 7,085,351 B2 | 8/2006 | Lu et al. | |
| 7,227,924 B2 | 6/2007 | Zhou et al. | |
| 7,359,484 B2 | 4/2008 | Qiu et al. | |
| 7,428,298 B2 | 9/2008 | Bard et al. | |
| 7,751,528 B2 | 7/2010 | Zhou et al. | |
| 8,576,988 B2 * | 11/2013 | Lewalter | A61B 6/4028 378/126 |
| 8,670,521 B2 * | 3/2014 | Bothorel | A61B 6/14 378/205 |
| 9,036,775 B2 * | 5/2015 | Yoshikawa | A61B 6/145 378/38 |
| 9,299,190 B2 | 3/2016 | Koivisto et al. | |
| 9,782,136 B2 * | 10/2017 | Zhou | A61B 6/145 |
| 2001/0019601 A1 | 9/2001 | Tkahashi et al. | |
| 2002/0006489 A1 | 1/2002 | Goth et al. | |
| 2002/0085674 A1 | 7/2002 | Price et al. | |
| 2002/0110996 A1 | 8/2002 | Yaniv et al. | |
| 2002/0140336 A1 | 10/2002 | Stoner et al. | |
| 2002/0171357 A1 | 11/2002 | Sun et al. | |
| 2003/0002627 A1 | 1/2003 | Espinosa et al. | |
| 2003/0102222 A1 | 6/2003 | Zhou et al. | |
| 2003/0198318 A1 | 10/2003 | Price et al. | |
| 2004/0028183 A1 | 2/2004 | Lu et al. | |
| 2004/0036402 A1 | 2/2004 | Keesmann et al. | |
| 2004/0108298 A1 | 6/2004 | Gao | |
| 2004/0114721 A1 | 6/2004 | Qiu et al. | |
| 2004/0240616 A1 | 12/2004 | Qiu et al. | |
| 2004/0256975 A1 | 12/2004 | Gao et al. | |
| 2005/0028554 A1 | 2/2005 | Wanner et al. | |
| 2005/0133372 A1 | 6/2005 | Zhou et al. | |
| 2005/0175151 A1 | 8/2005 | Dunham et al. | |
| 2005/0226371 A1 | 10/2005 | Kautzer et al. | |
| 2005/0226375 A1 | 10/2005 | Eberhard et al. | |
| 2005/0269559 A1 | 12/2005 | Zhou et al. | |
| 2005/0281379 A1 | 12/2005 | Qiu et al. | |
| 2007/0009081 A1 | 1/2007 | Zhou et al. | |
| 2007/0009088 A1 | 1/2007 | Edic et al. | |
| 2015/0359504 A1 | 12/2015 | Zhou et al. | |
| 2016/0193482 A1 * | 7/2016 | Fahrig | A61N 5/1078 600/1 |

FOREIGN PATENT DOCUMENTS

| | | |
|---|---|---|
| CN | 105411620 A | 3/2013 |
| DE | 19700992 | 7/1998 |
| DE | 10164315 A1 | 8/2002 |
| DE | 10164318 A1 | 8/2002 |
| JP | 53103392 | 9/1978 |
| JP | S54027793 | 2/1979 |

(56) References Cited

FOREIGN PATENT DOCUMENTS

| | | |
|---|---|---|
| JP | 57162431 A2 | 10/1982 |
| JP | H09-180894 | 2/1985 |
| JP | 60254615 A2 | 12/1985 |
| JP | S61-142644 | 6/1986 |
| JP | 06163381 A2 | 6/1994 |
| JP | 08038466 | 2/1996 |
| JP | 08264139 | 10/1996 |
| JP | 09180894 | 7/1997 |
| JP | H10161324 | 6/1998 |
| JP | 2000251826 A2 | 2/1999 |
| JP | 11-111158 | 4/1999 |
| JP | H11-116218 | 4/1999 |
| JP | 11-260244 | 9/1999 |
| JP | 2002-208028 | 7/2000 |
| JP | 2001-048509 | 2/2001 |
| JP | 2001190550 | 7/2001 |
| JP | 2001250496 | 9/2001 |
| TW | 00319886 | 11/1997 |
| TW | 0379354 B | 1/2000 |
| TW | 0439303 B | 6/2001 |
| TW | 0527624 B | 4/2003 |
| TW | 0529050 B | 4/2003 |
| TW | I307110 | 3/2009 |
| WO | WO 00/51936 A3 | 9/2000 |
| WO | WO 02/03413 | 1/2002 |
| WO | WO 02/31857 | 4/2002 |
| WO | WO 03/012816 A2 | 2/2003 |
| WO | WO 2006116365 A2 | 11/2006 |

OTHER PUBLICATIONS

Bonard, et al., "Field emission from single-wall carbon nanotube films," Appl. Phys. Lett., vol. 73, No. 7, pp. 918-920 (Aug. 17, 1998).

C. Bower, et al., "Synthesis and structure of pristine and alkali-metal-intercalated single-walled carbon nanotubes," Appl. Phys., A 67, pp. 47-52 (1998).

A.M. Cassell, et al., "Large Scale CVD Synthesis of Single-Walled Carbon Nanotubes," J. Phys. Chem., B 103, pp. 6484-6492 (Jul. 20, 1999).

de Heer, et al., "A Carbon Nanotube Field-Emission Electron Source," Science, vol. 270, pp. 1179-1180 (Nov. 17, 1995).

J.T. Dobbins and D.J. Godfrey, Digital X-ray tomosynthesis: current state of the art and clinical potential. Phys. Med. Biol., 2003. 48: p. 65-106.

Geis, et al., "Diamond emitters fabrication and theory," J. Vac. Sci. Technol. B, vol. 14, No. 3, pp. 2060-2067, May/Jun. 1996.

Raj Groenhuis, RL Webber, and U. Ruttimann, Computerized tomosynthesis of dental tissues. Oral Surg Oral Med Oral Pathol, 1983. 56: p. 206-214.

C. Journet, et al., "Large-scale production of single-walled carbon nanotubes by the electric-arc technique," Nature, vol. 388, pp. 756-760 (Aug. 21, 1997).

Kumar, et al., "Diamond-based field emission flat panel displays," Solid State Technology, vol. 38, pp. 71-74 (May 1995).

Liang Li, et al., x-ray digital intra-oral tomosynthesis for quasi-three-dimensional imaging: system, reconstruction algorithm, and experiments. Optical Engineering, 2013. 52(1): p. 013201.

Okano, et al., "Electron emission from nitrogen-doped pyramidal-shape diamond and its battery operation," Appl. Phys. Lett., vol. 70, No. 16, pp. 2201-2203 (Apr. 21, 1997).

Okano, et al., "Fabrication of a diamond field emitter array," Appl. Phys. Lett., vol. 64, No. 20, pp. 2742-2744 (May 16, 1994).

Okazaki, et al., "A New Emission Spectrum of Au2 in the Gas Evaporation Technique: 761-809 nm," Jpn. J. Appl. Phys., vol. 37, Pt. 1, No. 1, pp. 349-350 (Jan. 1998).

Radiologic Science for Technologist, Physics, Biology, and Protection, 6th Edition, S.C. Bushong, Mosby, Inc., 1997 (excerpt relating to focusing and thermionic emission).

Rinzler, et al., "Unraveling Nanotubes: Field Emission from an Atomic Wire," Science, vol. 269, pp. 1550-1553 (Sep. 15, 1995).

X.P. Tang, et al., "Electronic Structures of Single-Walled Carbon Nanotubes Determined by NMR," Science, vol. 288, pp. 492-494 (Apr. 21, 2000).

A. Thess, et al., "Crystalline Ropes of Metallic Carbon Nanotubes," Science, vol. 273, pp. 483-487 (Jul. 26, 1996).

Wang, et al., "Field emission from nanotube bundle emitters at low fields," Appl. Phys. Leff., vol. 70, No. 24, pp. 3308-3310 (Jun. 16, 1997).

Wang, et al., "A nanotube-based field-emission flat panel display," Appl. Phys. Lett., vol. 72, No. 2, pp. 2912-2913 (Jun. 1, 1998).

RL Webber, et al., Comparison of film, direct digital, and tuned-aperture computed tomography images to identify the location of crestal defects around endosseous titanium implants. Oral Surg Oral Med Oral Pathol Oral Radiol Endod 1996. 81: p. 480-490.

RL Webber, SE Webber, and J. Moore, Hand-held three-dimensional dental x-ray system: technical description and preliminary results. Dentomaxillofacial Radiology, 2002. 31: p. 240.

Yagishita, et al., "Effects of Cleavage on Local Cross-Sectional Stress Distribution in Trench Isolation Structure," Jpn. J. Appl. Phys., vol. 36, pp. 1335-1340 (Mar. 1997).

W. Zhu, et al., "Large Current Density from Carbon Nanotube Filed Emitters," Appl. Phys. Lett., American Institute of Physics, vol. 75, No. 6, Aug. 9, 1999, pp. 873-875.

Zhu, et al., "Low-Field Electron Emission from Updoped Nanostructured Diamond," Science, vol. 282, 1471-1473 (Nov. 20, 1998).

Christoph M. Ziegler and M. Franetzki, Digital tomosynthesis—experiences with a new imaging device for the dental field. Clin Oral Invest, 2003. 7: p. 41-45.

Non-Final Office Action for U.S. Appl. No. 09/679,303 dated Jan. 16, 2002.

Final Office Action for U.S. Appl. No. 09/679,303 dated May 6, 2002.

Non-final Office Action for U.S. Appl. No. 09/679,303 dated Aug. 20, 2002.

Notice of Allowance for U.S. Appl. No. 09/679,303 dated Nov. 1, 2002.

Office Communication for U.S. Appl. No. 09/679,303 dated Feb. 6, 2003.

International Search Report for Application No. PCT/US03/00537 dated Apr. 10, 2003.

Non-Final Office Action for U.S. Appl. No. 10/309,126 dated May 22, 2003.

Non-Final Office Action for U.S. Appl. No. 10/051,183 dated Sep. 10, 2003.

Non-Final Office Action for U.S. Appl. No. 10/309,126 dated Nov. 5, 2003.

Non-Final Office Action for U.S. Appl. No. 10/309,126 dated Apr. 20, 2004.

Non-Final Office Action for U.S. Appl. No. 10/051,183 dated Apr. 21, 2004.

Notice of Allowance for U.S. Appl. No. 10/309,126 dated Aug. 26, 2004.

Notice of Allowance for U.S. Appl. No. 10/051,183 dated Aug. 31, 2004.

Corrected Notice of Allowance for U.S. Appl. No. 10/309,126 dated Sep. 14, 2004.

Non-Final Office Action for U.S. Appl. No. 10/358,160 dated Sep. 21, 2004.

Office Communication for U.S. Appl. No. 10/051,183 dated Jan. 14, 2005.

Non-Final Office Action U.S. Appl. No. 10/358,160 dated Jun. 7, 2005.

Restriction Requirement U.S. Appl. No. 10/358,160 dated Oct. 26, 2005.

Notice of Allowance U.S. Appl. No. 10/358,160 dated Feb. 8, 2006.

International Search Report for Application No. PCT/US05/03991 dated Jun. 22, 2006.

Restriction Requirement for U.S. Appl. No. 11/051,332 dated Sep. 7, 2006.

(56) References Cited

OTHER PUBLICATIONS

Notice of Allowance dated for U.S. Appl. No. 11/051,332 dated Dec. 28, 2006.
Korean Office Action for Korean Patent Application No. 10-2004-7011373 dated Jun. 11, 2007.
Korean Office Action for Korean Patent Application No. 10-2003-700004987 dated Jul. 19, 2007.
European Examination Report for European Patent Application No. 03702044.3 dated Jun. 28, 2007.
Chinese Office Action for Patent Application No. 03806739.0 dated Oct. 19, 2007.
Non-Final Office Action for U.S. Appl. No. 11/415,953 dated Dec. 11, 2007.
Korean Office Action for Korean Patent Application No. 10-2004-7011373 dated Dec. 18, 2007.
Taiwanese Office Action for Taiwan Patent No. 093102622 dated Dec. 21, 2007.
European Examination Report for European Patent Application No. 03702044.3 dated Mar. 3, 2008.
Chinese Office Action for Chinese Patent Application No. 01820211.X (PCT/US01/30027) dated Mar. 14, 2008.
Non-Final Office Action for U.S. Appl. No. 10/970,384 dated Apr. 8, 2008.
Notification of non-acceptance of amended claims from Chinese Patent Office for Chinese Patent Application No. 03806739.0 (PCT/US03/00537) dated Apr. 25, 2008.
Restriction Requirement for U.S. Appl. No. 11/415,953 dated May 22, 2008.
Canadian Office Action for Canadian Application No. 2,424,826 dated May 27, 2008.
Japanese Office Action for Japanese Patent Application No. 2003-562962 for corresponding PCT No. US03/00537 dated Jun. 20, 2008.
Japanese Office Action for Japanese Patent Application No. 2003-580561 for corresponding PCT No. US03/06345 dated Sep. 3, 2008.
Chinese Grant Decision for Chinese Patent Application No. 01820211 (PCT/US01/30027) dated Sep. 26, 2008.
International Search Report and Written Opinion for PCT Application No. PCT/US08/70477 dated Oct. 1, 2008.
Japanese Office Action for Japanese Patent Application No. 2002-535152, based on PCT/US01/30027 dated Oct. 17, 2008.
Chinese Patent Issue Confirmation for Application No. ZL01820211.X corresponding to PCT/US01/30027 dated Feb. 4, 2009.
Chinese Notice of Publication for Chinese Patent Application No. 200810215733.1 dated Feb. 13, 2009.
Chinese Notice of Grant for Application No. 093102622 dated Mar. 1, 2009.
Japanese Final Office Action Notification for Application No. 2003-562962 based on PCT/US03/00537 dated Mar. 30, 2009.
Chinese Office Action for Application No. 200710003710.X dated May 8, 2009.
Final Office Action for U.S. Appl. No. 11/441,281 dated Jun. 4, 2009.
Supplementary European Search Report for European Patent Application No. 01981327.8 dated Jun. 22, 2009.
Non-Final Office Action for U.S. Appl. No. 12/176,056 dated Sep. 2, 2009.
Japanese Office Action for Japanese Patent Application No. 2002-535152 dated Dec. 7, 2009.
Chinese Rejection Decision for Chinese Application No. 200710003710.X dated Dec. 11, 2009.
Notice of Allowance for U.S. Appl. No. 12/176,056 dated Apr. 2, 2010.
Non-Final Office Action for U.S. Appl. No. 14/741,041 dated Aug. 18, 2016.
Final Office Action for U.S. Appl. No. 14/741,041 dated Apr. 26, 2017.
Notice of Allowance for U.S. Appl. No. 14/741,041 dated Jul. 17, 2017.
German Office Action for German Application No. 112008001902 dated Sep. 15, 2017.

* cited by examiner

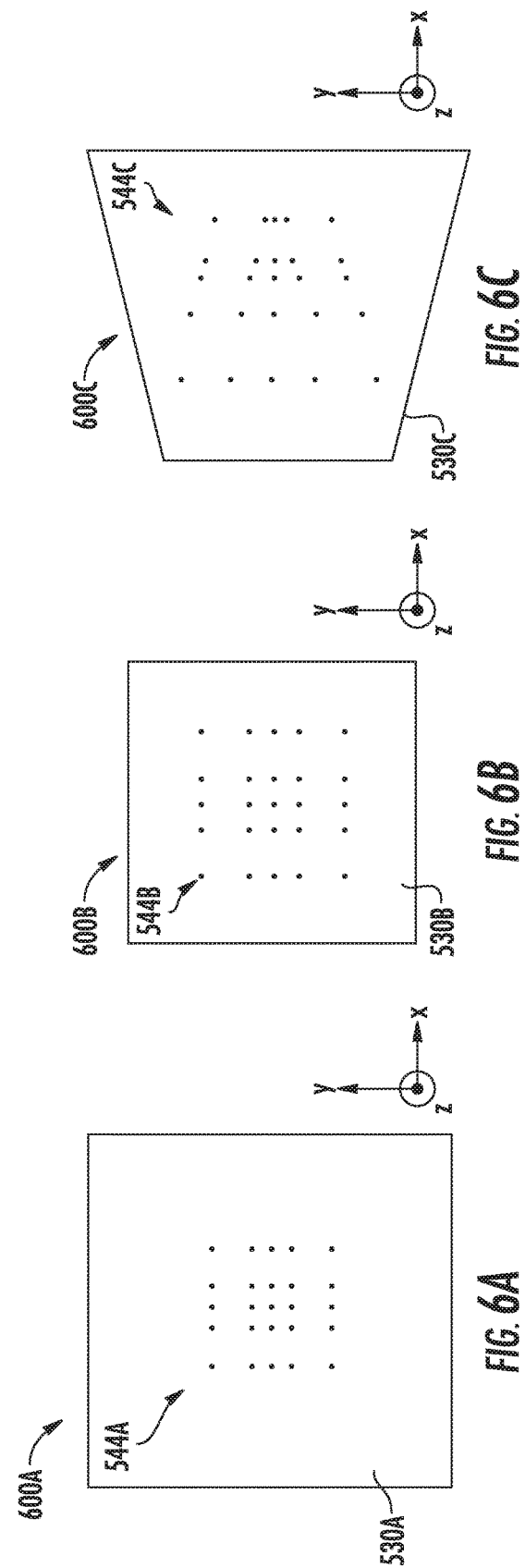

DIGITAL TOMOSYNTHESIS SYSTEMS, METHODS, AND COMPUTER READABLE MEDIA FOR INTRAORAL DENTAL TOMOSYNTHESIS IMAGING

CROSS-REFERENCE TO RELATED APPLICATIONS

This patent application is a continuation of and claims priority to U.S. patent application Ser. No. 14/741,041, filed Jun. 16, 2015, which claims priority to both U.S. Provisional Application Ser. No. 62/013,181, filed Jun. 17, 2014, and to U.S. Provisional Application Ser. No. 62/143,443, filed Apr. 6, 2015, each of which are incorporated by reference herein in their entireties.

TECHNICAL FIELD

The subject matter disclosed herein relates to x-ray radiography. More particularly, the subject matter disclosed herein relates to digital tomosynthesis systems, methods, and computer readable media for intraoral dental tomosynthesis imaging.

INCORPORATION BY REFERENCE

U.S. Pat. No. 7,751,528 filed on Jul. 18, 2008, claiming priority to U.S. Provisional Application No. 60/961,175 filed on Jul. 19, 2007, is hereby incorporated by reference as if set forth in its entirety herein,

BACKGROUND

Since x-rays were first discovered, dental radiology has seen several milestones. These include the development of panoramic radiography, dental tomography, dental tomosynthesis, more efficient image detectors, computerized dental radiography and, most recently, cone-beam computed tomography (CBCT). CBCT has found wide acceptance in the dental community because of its ability to provide a three-dimensional (3D) representation of the hard tissues of the oral and maxillofacial region. While CBCT has been shown useful for many applications, it has not shown to improve caries detection. In part, this is the result of the beam hardening artifacts that occur in teeth. These artifacts may obscure existing caries lesions or may induce false-positive diagnoses. Even a high-resolution CBCT system with a small field-of view was shown not to improve the detection of proximal caries lesions.

Intraoral radiography is the mainstay of dental imaging. It provides relatively high resolution, and limited field of view images for most routine dental needs. However, as a two-dimensional (2D) imaging modality, the technique suffers from superimposition of overlying structures and loss of spatial information in the depth dimension. Panoramic imaging, a popular form of extra-oral imaging, visualizes the entire maxilla, mandible, temporo-mandibular joints (TMJ) and associated structures in a single image, but it is subject to considerable geometric distortion and has relatively low spatial resolution compared with intraoral radiography. CBCT as a three-dimensional (3D) imaging modality has found wide acceptance in dentistry, especially for surgical planning procedures such as dental implant and orthodontic treatment planning, and evaluation of endodontic and pathological condition. There are, however, several disadvantages associated with CBCT in comparison to 2D radiography: (1) excess noise and artifacts from metal dental restorations/appliances reduce the image quality; (2) acquisition, reconstruction, and interpretation time are greatly increased, reducing clinical efficiency and increasing financial cost; and (3) significantly higher ionizing radiation doses increase radiation burden for the patient.

Despite the many technological advances, the radiographic diagnostic accuracy for some of the most common dental conditions has not improved in many years and in some cases remains low. Examples include caries detection, root fracture detection, and assessment of periodontal bone loss.

Caries is the most common dental disease. The World Health Organizations estimates that 60-90% of school children and nearly all adults have dental caries at some point in time. If carious lesions are detected early enough, i.e. before cavitation, they can be arrested and remineralized by non-surgical means. When carious lesions go undetected, they can evolve into more serious conditions that may require large restorations, endodontic treatment, and, in some cases, extractions. The detection sensitivity of caries has not seen any significant improvement in the past several decades. 2D intraoral radiography is the current gold standard, with a reported sensitivity ranging from 40% to 70% for lesions into dentine and from 30% to 40% for lesions confined to enamel. CBCT does not provide significant improvement for caries detection. Beam-hardening artifacts and patient movement decrease structure sharpness and definition.

The detection of vertical root fractures (VRF) represents a clinically significant diagnostic task with important ramifications in tooth management. VRFs are considered one of the most frustrating tooth conditions associated with endodontic therapy. Overall detection of VRFs remains poor. The ability of CBCT to detect initial small root fractures is limited by its relatively low resolution. Furthermore, excess beam hardening, streak artifact, and noise result in both significantly decreased sensitivity and increased false positive root fracture diagnosis.

Dental radiography provides important information for assessing tooth prognosis and making treatment decisions associated with periodontal disease. Conventional 2D intraoral radiography provides exceptionally high image detail of key dental structures, but because of structure superimposition delivers poor assessment of alveolar bone architecture and consistently underestimates bone loss. CBCT conversely delivers more accurate 3D assessment of clinically-relevant morphologic alveolar bone defects but with a penalty in image detail. Beam hardening and streak artifacts are a significant problem for accurate bone morphology characterization.

These diagnostic tasks illustrate the clinical need for a diagnostic imaging system with high resolution, 3D capabilities, reduced metal artifact and lower radiation burden to patients.

Digital tomosynthesis imaging is a 3D imaging technique that provides reconstruction slice images from a limited-angle series of projection images. Digital tomosynthesis improves the visibility of anatomical structures by reducing visual clutter from overlying normal anatomy. Some examples of current clinical tomosynthesis applications include chest, abdominal, musculoskeletal, and breast imaging. For example, an industrial prototype extra-oral tomosynthesis scanner may use a dental x-ray tube operating at 60 peak kilovoltage (kVp) and 7 milliampere (mA), and an exposure time of 0.4 seconds (s) for each projection image. The scanning time may be 40 s. A set of 24 radiographs may be taken in a circular scanning geometry with a total of 22 degrees (°) coverage. A system resolution may be 5 lines per millimeter (lp/mm) and a reconstruction slice thickness may be 1 mm. A total absorbed dose for the 24 projections may be 16 milligray (mGy), corresponding to a maximum body dose of 16 millisievert (mSv), close to that from a panoramic scan of 12 mGy. Notably, such a dose is lower than that used in CT. In this manner, it may be concluded that tomosynthesis offers higher spatial resolution and less radiation compared to CT and is less expensive.

Digital tomosynthesis has been applied to dental imaging in the past. A variation of the tomosynthesis technique, called Tuned Aperture Computed Tomography (TACT), was investigated in the late 1990's for dental imaging. TACT significantly improved the diagnostic accuracy for a number of tasks compared to conventional radiography. These included: (1) root fracture detection, (2) detection and quantification of periodontal bone loss, (3) implant site assessment, and (4) the evaluation of impacted third molars. The results for caries however were inconclusive.

TACT was not adopted clinically because the technology was not practical for patient imaging. Conventional x-ray tubes are single pixel devices where x-rays are emitted from a fixed point (focal spot). To acquire the multiple projection images, an x-ray source was mechanically moved around the patient. A fiduciary marker was used to determine the imaging geometry. The process was time consuming (e.g., approximately 30 minutes per scan) and required high operator skill to accomplish image acquisition.

Intraoral tomosynthesis imaging has also been considered. For example, a hand-held tuned-aperture computed tomography system with an intraoral x-ray detector, such that a dental x-ray source is mechanically moved to different locations with respect to the detector to produce multiple projection images for the reconstruction may be utilized. In such a case, a fiducial marker is used to track the positions of the x-ray source relative to the detector. Alternatively, an intraoral tomosynthesis scanner with a conventional dental x-ray tube mounted on a mechanical rotating gantry may also be used. The tube is mechanically moved to the different locations along the arc to generate the different projection images.

Compared to intraoral systems, extra-oral devices require higher radiation exposure for the patients, an image quality that is affected by out-of-focus structures due to incomplete blurring of an opposing jaw, and significant beam hardening artifacts. For example, extra-oral tomosynthesis has been investigated in a patient study using an experimental device, and using CBCT. The extra-oral geometry required high radiation dose. The image quality was compromised by cross-talk of out-of-focus structures. Intraoral tomosynthesis using a single mechanically scanning x-ray source has been described in the patent literature, and investigated in a recent publication using a single conventional x-ray source and a rotating phantom.

One common limitation of the current tomography system including tomosynthesis is that the x-ray source and/or the detector must be moved to different viewing angles to generate the projection views needed for reconstruction. This is because most of the conventional x-ray tubes contain either one or two focal spots where the x-ray radiation is emitted. To illuminate the object from different directions, the source, the detector, or the object needs to be rotated or translated. The mechanical motion of the gantry limits the scanning speed and resolution, and thereby makes the system large and less mobile.

Spatially distributed x-ray arrays with multiple x-ray focal spots are now commercially available from manufacturers including XinRay Systems. These source arrays can electronically generate a scanning x-ray beam from different locations or focal spots without any mechanical motion.

One example is the carbon nanotube based field emission x-ray source array that utilizes an array of individually controllable electron emitters such as the carbon nanotubes (CNTs) as the 'cold cathodes' to generate electrons which are accelerated to bombard the anode to produce x-ray radiations. By electronically switching on and off the individual CNT cathodes, a scanning x-ray beam is generated from each different focal spots on the x-ray anode.

The CNT x-ray source array is particularly attractive for tomography imaging. By generating projection views from different angles without mechanical motion, it enables stationary tomography with faster scanning speed and higher resolution. The flexibility in the source configuration also opens up the feasibility of designing tomography scanners with novel geometries.

A stationary digital breast tomosynthesis (s-DBT) system has been disclosed in U.S. Pat. No. 7,751,528 and the Chinese application 200880107680.X "Stationary x-ray digital breast tomosynthesis systems and related methods", incorporated by reference herein, which also discloses the general concept of stationary digital. The stationary design increases the system spatial resolution by eliminating the image blurring caused by x-ray tube motion. A faster scan time is achieved by integrating with a high-frame-rate detector to minimize patient motion and discomfort under compression. The stationary design without the constraint of mechanical motion also allows a wider angle tomosynthesis scan for better depth resolution without changing the scanning time.

Additionally, feasibility of stationary chest tomosynthesis has recently been investigated using a linear CNT x-ray source array.

SUMMARY

Digital tomosynthesis systems, methods, and computer readable media for intraoral dental tomosynthesis imaging are provided. In some aspects, an intraoral tomosynthesis imaging system comprises an x-ray source array for positioning outside a mouth of a patient, wherein the x-ray source array contains multiple x-ray focal spots that are spatially distributed on an anode; an area digital x-ray detector for positioning inside the mouth of the patient; a geometry calibration mechanism for connecting the area digital x-ray detector to the x-ray source array; an x-ray collimator for confining x-ray beams to a region of interest (ROI); a controller for regulating x-ray radiation and synchronization of the x-ray radiation with the area digital x-ray detector, such that multiple two-dimensional (2D) projection images of the ROI are acquired without mechanical motion of the x-ray source array, the area digital x-ray detector, or the mouth of the patient; and a computer program and workstation for three-dimensional (3D) tomosynthesis image reconstruction and display.

In other aspects, an intraoral three-dimensional (3D) imaging system comprises an x-ray source array for positioning outside a mouth of a patient, wherein the x-ray source array contains 3 to 25 x-ray focal spots that are spatially distributed on an anode, each of the x-ray focal spots being approximately between 0.2 and 2 mm in size and spanning an angular range approximately between 3 and 25 degrees; an area digital x-ray detector for positioning inside the mouth of the patient; a geometry calibration mechanism connectable to the area digital x-ray detector; an x-ray collimator for confining x-ray beams to a region of interest (ROI); an electronic controller for regulating x-ray radiation and synchronization of the x-ray radiation with the area digital x-ray detector such that multiple two-dimensional (2D) projection images of the ROI are acquired without mechanical motion of the x-ray source array, the area digital x-ray detector, or the mouth of the patient; and a computer workstation with executable programs for geometry calibration, tomosynthesis reconstruction, and image display.

In further aspects, a method for intraoral three-dimensional (3D) tomographic imaging comprises positioning an x-ray source array outside a mouth of a patient, wherein the x-ray source array comprises multiple x-ray focal spots that are spatially distributed on an anode; positioning an area digital x-ray detector at a first position inside the mouth of the patient; connecting a geometry calibration mechanism to the area digital x-ray detector; collimating x-ray beams from all of the multiple x-ray focal spots to a same region of interest (ROI); acquiring a first set of two-dimensional (2D) projection images of the mouth of the patient at the first position; and processing the first set of 2D projection images to obtain a reconstructed 3D tomography image of the ROI for display and analysis.

In still further aspects, a non-transitory computer readable medium comprising computer executable instructions that when executed by a processor of a computer control the computer to perform a method comprises positioning an x-ray source array outside a mouth of a patient, wherein the x-ray source array comprises multiple x-ray focal spots that are spatially distributed on an anode; positioning an area digital x-ray detector at a first position inside the mouth of the patient; connecting a geometry calibration mechanism to the area digital x-ray detector; collimating x-ray beams from all of the multiple x-ray focal spots to a same region of interest (ROI); acquiring a first set of two-dimensional (2D) projection images of the mouth of the patient at the first position; and processing the first set of 2D projection images to obtain a reconstructed 3D tomography image of the ROI for display and analysis.

In still further aspects, a geometry calibration mechanism for motion correction during tomography image acquisition using an x-ray imaging system comprises a visible light laser source attached to an x-ray source array, wherein the visible light laser source comprises a pre-determined frequency and wavelength; a one-dimensional (1D) or two-dimensional (2D) optical diffraction grating with known diffraction line spacing between grating lines, the 1D or 2D optical diffraction grating being attached to the x-ray source array at a known relative position; a screen positioned outside a mouth of a patient and attached to an x-ray detector at a known relative position; a camera attached to the x-ray source array for capturing an image of the visible light diffraction spots projected onto the screen; and a computer program configured to analyze a relative position of the visible light diffraction spots on the screen.

Although some of the aspects of the subject matter disclosed herein have been stated hereinabove, and which are achieved in whole or in part by the presently disclosed subject matter, other aspects will become evident as the description proceeds when taken in connection with the accompanying drawings as best described hereinbelow.

BRIEF DESCRIPTION OF THE DRAWINGS

Features and advantages of the present subject matter will be more readily understood from the following detailed description which should be read in conjunction with the accompanying drawings that are given merely by way of explanatory and non-limiting example, and in which:

FIGS. 6A-6C are schematic views illustrating exemplary light patterns using the geometry calibration device of FIGS. 5A-5D;

DETAILED DESCRIPTION

The present subject matter provides intraoral tomosynthesis systems, methods, and computer readable media for dental imaging applications, although such geometry calibration devices, tomosynthesis systems, and methods can be used for applications other than dental imaging. For example, a stationary digital breast tomosynthesis (s-DBT) system is disclosed in U.S. Pat. No. 7,751,528, the entirety of which is incorporated by reference herein. Notably, the stationary design of the s-DBT system increases the system spatial resolution by eliminating the image blurring caused by x-ray tube motion. A faster scan time is also achieved by integrating with a high-frame-rate detector to minimize patient motion and discomfort under compression. The stationary design of the s-DBT system, without the constraint of mechanical motion, also allows a wider angle tomosynthesis scan for better depth resolution without changing scanning time.

In some aspects, the stationary tomosynthesis system is for dental imaging applications. Specifically, the stationary tomosynthesis system may be for intraoral imaging applications using an x-ray detector placed inside a mouth of a patient. In other aspects, the stationary tomosynthesis system may be for extra-oral imaging applications using an x-ray detector placed outside the mouth of the patient.

In some aspects, the stationary tomosynthesis system is a dual energy tomosynthesis system. For example, for each object being imaged, two complete sets of x-ray projection images can be collected. A first set can be collected at a first x-ray energy, while a second set can be collected at a second x-ray energy, where the first x-ray energy is different from the second x-ray energy. In one aspect, the two sets of x-ray images can be collected at two different x-ray anode voltages, and then processed, reconstructed, and subtracted to enhance contrast for certain features, such as, for example, caries. In another aspect, at each viewing angle, two projection images can be acquired, one at a first x-ray energy, the other at a second x-ray energy.

Figure 1:
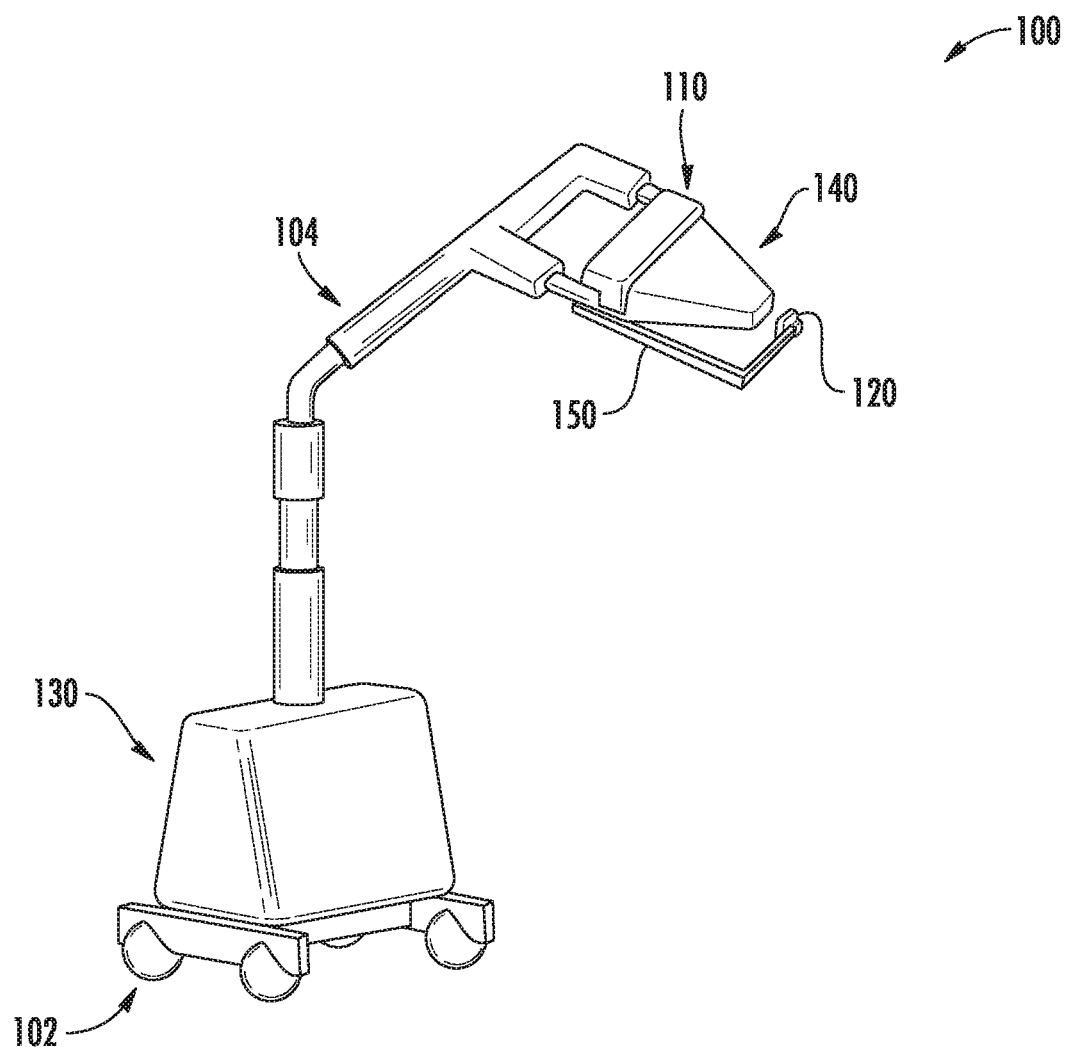
FIG. 1 is a perspective view illustrating a digital tomosynthesis system with a fixed linkage between an x-ray source and an x-ray detector according to some embodiments of the present subject matter.

Accordingly, the present subject matter provides a stationary intraoral tomosynthesis system comprising an x-ray source, an x-ray detector for positioning inside a mouth of a patient, a geometry calibration device, and control electronics for obtaining multiple projection views of a region of interest (ROI) of an object (e.g., teeth of a patient) without having to move any of the x-ray source, the x-ray detector, or the ROI. FIG. 1 illustrates one such embodiment of the intraoral tomosynthesis system, generally designated 100. System 100 may comprise an x-ray source 110 disposed in a vacuum and/or an oil chamber (not shown), an x-ray detector 120, control electronics 130, a collimator 140, and an x-ray detector holding mechanism 150. In some aspects, system 100 may be mounted, such that it is immobile. For example, system 100 can be mounted from a ceiling, a wall, etc. In other aspects, system 100 may be a mobile or otherwise portable digital tomosynthesis system. For example, system 100 can comprise wheels, may be placed on a mobile cart, hand truck, stand, etc. FIG. 1 illustrates a mobile cart 102 on which system 100 is attached using, for example, a mechanical arm 104. Mechanical arm 104 may be rotationally and axially movable about a pivot or hinge joint in order to adjust system 100 about an object to be imaged. Thus, using mobile cart 102 and mechanical arm 104, system 100 may be freely moved and rotated for optimal positioning. Optionally, mobile cart 102 may comprise a rechargeable battery (not shown) that may provide power for imaging, thereby obviating the need for electrical cords and/or wires for power.

X-ray source 110 may be configured to direct x-ray beams (e.g., 108, FIG. 2A) towards a location or position at which an ROI of an object (e.g., teeth of a patient) is placed. The x-ray beams can be directed towards the location or position from several different angles. Further, x-ray source 110, x-ray detector 120, and the object can be positioned such that the generated x-ray beams are detected by x-ray detector 120. In some aspects, x-ray source 110 may comprise a spatially distributed x-ray source array positioned in such a manner that the generated x-ray beams are directed substantially towards the object and can pass through the ROI of the object. In some aspects, the ROI of the object can change as different ROIs of the same object may be imaged during one or more imaging sessions.

In some aspects, the x-ray source array of the x-ray source 110 may include multiple, individually programmable x-ray pixels spatially distributed as a linear array, which enables tomosynthesis imaging with a stationary design. Alternatively, the x-ray pixels may be distributed non-linearly as, for example, an arc, a circumference of a circle or a polygon, in a two dimensional matrix, etc., along x-ray source 110. In some aspects, the x-ray pixels in the array may be evenly spaced and/or angled for directing x-ray beams towards the ROI of the object. Regardless, the x-ray pixels may be arranged in any suitable position such that the x-ray beams are directed substantially towards the object and the x-ray beams are detected by x-ray detector 120. Notably, x-ray source 110 and x-ray detector 120 can be stationary with respect to one another during irradiation of the object by x-ray source 110 and detection by x-ray detector 120. X-ray source 110 can be controlled (e.g., by control electronics 130) for sequential activation (i.e., one pixel being activated at a time) for a predetermined dwell time and predetermined x-ray dose.

In some aspects, the x-ray source array of source 110 can, for example, comprise between 5 and 100 pixels (e.g., 10 and 100 pixels); in particular, 25 pixels. Each pixel can comprise, for example, a carbon nanotube (CNT) field emission based cathode, such as those commercially available from manufacturers including, for example, XinRay Systems Inc, a gate electrode to extract the electrons, and a set of electron focusing lenses (e.g., EinZel type electrostatic focusing lenses) to focus the field emitted electrons to a small area or focal spot on a target (e.g. an anode). Notably, a CNT cathode is a cold cathode that can be switched on and off instantly. Using a CNT cathode in this manner can reduce warm up of source 110 and heat generation as compared to traditional vacuum electronics based on thermionic cathodes (e.g., cathode ray tubes, microwave tubes, X-ray tubes, etc). Alternatively, each pixel can comprise a thermionic cathode, a field emission cathode, a photocathode, etc. Regardless, in some aspects, each cathode can have a corresponding focal spot. The x-ray focal spots are distributed in space so that the x-ray radiation emitted from the focal spots irradiates the ROI from different viewing angles.

In some aspects, where the x-ray source pixels are arranged linearly parallel to the detector plane, rather than an arc, the pixel-to-source distance can vary from pixel to pixel. In order to compensate for this variation in x-ray beam traveling distance, x-ray tube current from each pixel can be individually adjusted such that flux at a phantom surface remains the same.

Sizes of focal spots and/or x-ray flux generated by each pixel of the x-ray source array of x-ray source 110 can be adjusted by control electronics 130. For example, control electronics 130 may comprise an electronic controller configured to regulate x-ray radiation and synchronization of the x-ray radiation with the area digital x-ray detector such that multiple 2D projection images of the ROI are acquired without mechanical motion of the x-ray source array, the area digital x-ray detector, or the mouth of the patient, by switching x-ray radiation on and off at each focal spot for a pre-determined dwell time and regulates the intensity of the x-ray flux from each focal spot. X-ray source 110 is electronically interfaced with x-ray detector 120 such that 2D projection image is recorded with the x-ray radiation originated from each focal spot. Electronic controller 130 can regulate the intensity from each focal spot by either directly reading the x-ray radiation from each focal spot, reading the x-ray tube current, or reading the cathode current. Alternatively, the focal spots can range between about 0.05 mm and 2 mm in size and can span an angular range at a given source-imager-distance, for example, a range between 5 and 25 degrees. System 100 can be designed for an isotropic 0.2×0.2 mm effective focal spot size for each x-ray source pixel. The individual focal spot size can be adjusted by adjusting the electrical potentials of the focusing electrodes. To minimize current fluctuation and delay and to reduce pixel to pixel variation, an electrical compensation loop can be incorporated to automatically adjust the gate voltage to maintain a constant pre-set emission current. The area of the CNT cathode can be selected such that a peak x-ray tube current of about 10 mA can be obtained with the effective focal spot size of 0.2×0.2 mm. Notably, a higher x-ray peak current of 50-100 mA can be obtained by increasing the CNT area and the focal spot size.

In some aspects, system 100 comprises x-ray detector 120, which can be configured for intraoral or extra-oral detection of projection images. For example, x-ray detector 120 can comprise an intraoral x-ray detector that is configured to be positioned behind teeth of a patient in an interior of the patient's mouth. X-ray detector 120 can comprise a fast frame rate, in the order of 1-100 frames-per-second, in particular, 1-10 frames-per-second. X-ray detector 120 can also comprise a high spatial resolution, with the pixel size in the range of 10×10 micron to 200×200 micron to detect projection images of the object (e.g. teeth within an interior of the patient's mouth). Thus, 2D projection images of the ROI can be acquired within approximately 10 seconds without mechanical motion of x-ray source 110, x-ray detector 120, or the object (e.g., mouth of the patient). In other aspects, system 100 is an extra-oral tomosynthesis imaging system with a distributed x-ray source array and an extra-oral detector. X-ray radiation is generated sequentially from the multiple x-ray focal spots without any mechanical motion to generate the projection views needed for image reconstruction.

X-ray detector 120 can be configured to collect projection images of the object from different angles for tomosynthesis. In order to do so, control electronics 130, which may be stored in a housing of system 100, can be configured to sequentially activate the x-ray source array of electron emitting pixels, as described herein, which are spatially distributed over an area of x-ray source 110 (e.g., on one or multiple anodes in an evacuated chamber (not shown)) for a pre-determined exposure time, radiation dose, and x-ray energy, and to regulate an intensity of x-ray flux from each focal spot. X-ray source 110 can electronically interface with x-ray detector 120 such that a projection image is recorded with the radiation originated from each focal spot. Notably, control electronics 130 can vary an intensity of the x-ray radiation based on a distance between the x-ray source array of x-ray source 110 and the object by directly reading the radiation from each focal spot, reading the x-ray tube current, or reading the cathode current. In this manner, the x-ray dose delivered to the object from every viewing angle is the same.

In some aspects, a size of each focal spot and/or the x-ray flux generated by x-ray source 110 can be adjusted by control electronics 130. For example, control electronics can adjust an x-ray source 110 comprising an x-ray tube that is configured to operate with x-ray photon energy up to 100 kVp (e.g., between 60 and 100 kVp), a tube current up to 10-20 mA (e.g., between 1-10 mA), and an exposure time per projection up to 500 milliseconds (e.g., between 10 and 500 ms), and with a focal spot size in the range of 0.1 mm to 1.5 mm to a higher x-ray peak current of 50-100 mA by increasing a carbon nanotube area and a focal spot size. In some aspects, control electronics 130 can also adjust the individual focal spot size by adjusting electrical potentials of the focusing electrodes. In some aspects, control electronics 130 can minimize current fluctuation and reduce pixel to pixel variation, by incorporating an electrical compensation loop to adjust the gate voltage to maintain a constant pre-set emission current.

Collimator 140 can be placed between a window of x-ray source 110 and detector 120 to confine the x-ray radiation to the ROI of the object. In some aspects, a first end of collimator 140 can be fixed to x-ray source 110, while a second end of collimator 140 can be collapsible.

In some embodiments, a mechanical fixture (e.g., x-ray detector holder) 150 can connectedly attach x-ray source 110 to x-ray detector 120 in a known and fixed position, which may be advantageous for tomosynthesis reconstruction. Thus, at all times a position of x-ray source 110 relative to x-ray detector 120 may be known. Alternatively, positions of the x-ray focal spots relative to x-ray detector 120 need not be determined by a physical connection between x-ray detector 120 and x-ray source 110. Instead, a geometry calibration device may be utilized to determine a position of x-ray source 110 relative to x-ray detector 120 and thereby detect positions of the x-ray focal spots relative to x-ray detector 120.

Figure 2A:
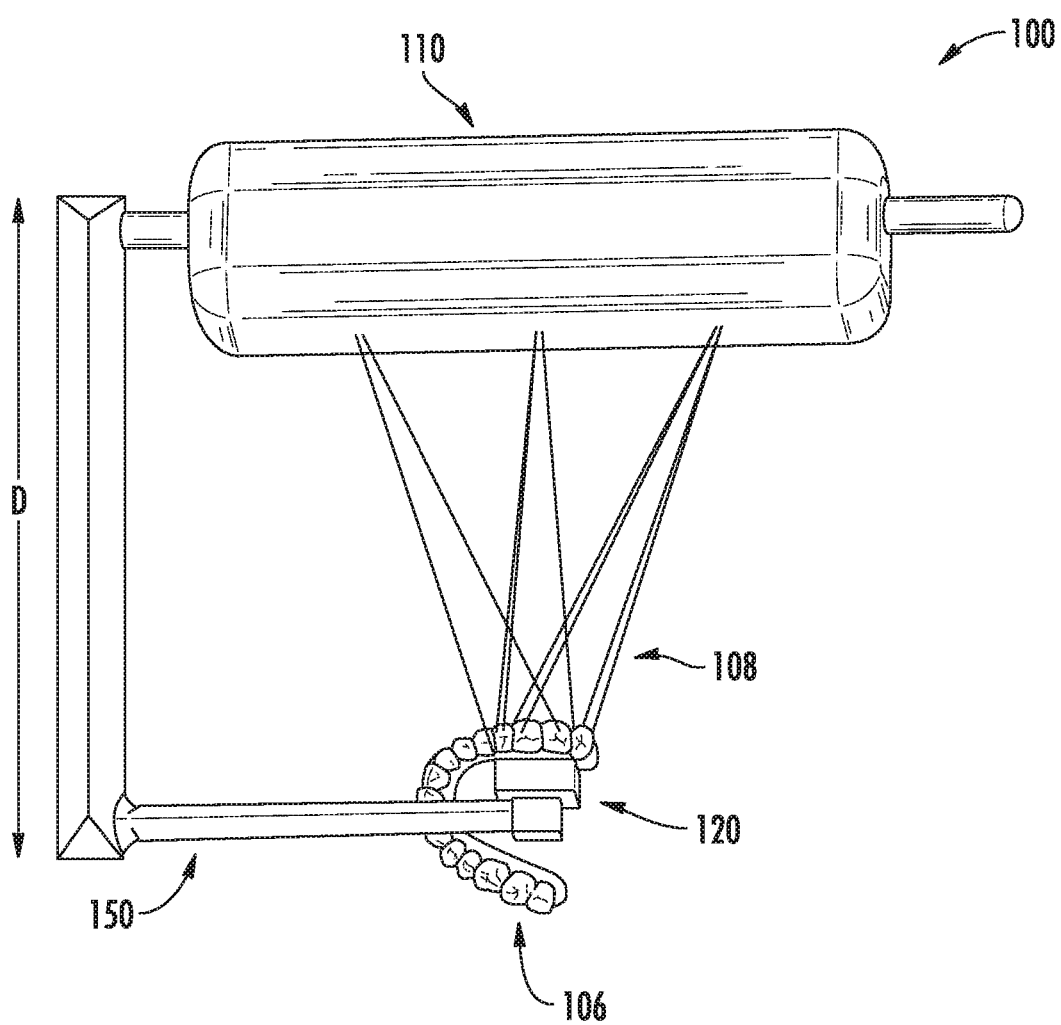
FIG. 2A is a top view illustrating the fixed linkage between the x-ray source and the x-ray detector of FIG. 1.

Referring to FIG. 2A, a more detailed view of system 100 is illustrated. In particular, the relationship between x-ray source 110, x-ray detector 120, and x-ray detector holder 150 is illustrated in a more detailed manner. As illustrated in FIG. 2A, x-ray detector holder 150 fixes x-ray source 110 to x-ray detector 120 at a known distance relative to one another. In some aspects, a first end of x-ray detector holder 150 is fixed to x-ray source 110, while a second end of x-ray detector holder 150 is fixed to x-ray detector 120. In some aspects, x-ray source array of source 110 comprises multiple pixels each positioned in a known location and set to point at a known angle inwards toward an object. Thus, when x-ray source 110 and x-ray detector 120 are disposed at a fixed distance apart from one another, exact positions of the focal spots generated by the x-ray source array pixels with respect to x-ray detector 120 will be known.

For example, in FIG. 2A, x-ray source 110 and x-ray detector 120 are fixedly separated a distance D by x-ray detector holder 150. In this example, x-ray source 110 comprises a linear x-ray source array and x-ray source detector 120 is configured as an intraoral detector for placement in a mouth of a patient in order to image teeth, generally designated 106, of the patient. X-ray detector 120 may be disposed behind a specific ROI of teeth 106. Accordingly, when x-ray source 110 is activated, x-ray beams, generally designated 108, may be generated and project through the ROI of teeth 106 and onto x-ray detector 120. Since distance D is a fixed and known quantity, exact positions of the focal spots generated by the x-ray source array pixels with respect to x-ray detector 120 may be known. In this manner, reconstruction of the 2D projection images into 3D images may be improved.

Figure 2B:
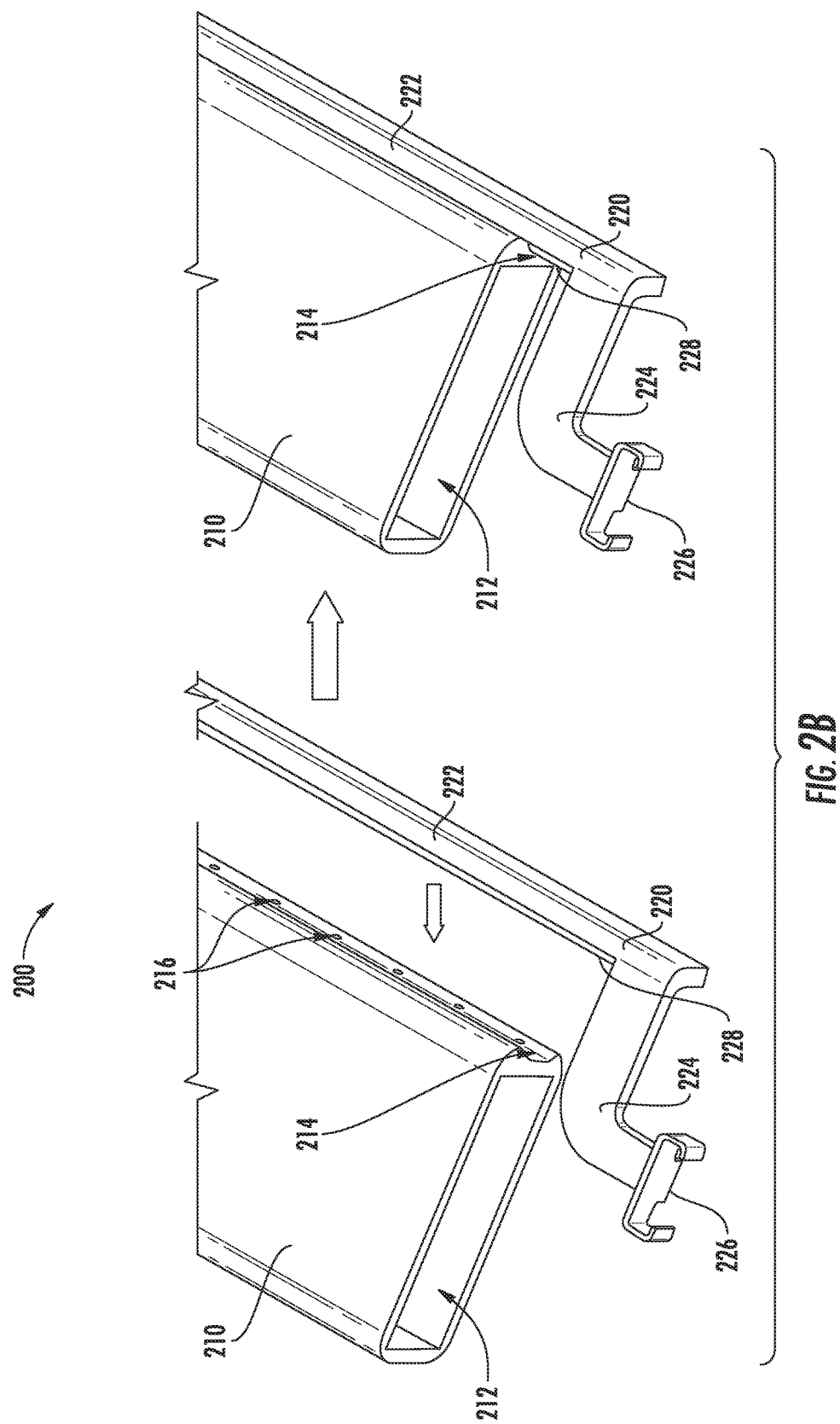
FIG. 2B is a top perspective view illustrating a receptacle between an x-ray source and an x-ray detector according to some embodiments of the present subject matter.

Referring to FIG. 2B, an alternative to x-ray detector holder 150 (see, FIGS. 1-2A) is illustrated. Specifically, a device 200 may be utilized to connect an x-ray source to an x-ray detector at a known distance relative to one another. In some aspects, device 200 can comprise a receptacle 210 attachable to an x-ray source and connectable with a connecting arm 220 attachable to an x-ray detector. Where device 200 is used in an intraoral tomosynthesis system (e.g., 100), receptacle 210 may be attachable to an x-ray source (e.g., 110) and may be magnetically connected with connecting arm 220, which may be attachable to an intraoral x-ray detector (e.g., 120) positioned within a mouth of a patient.

In some aspects, receptacle 210 may include any suitable material, for example, any metal or metallic material (e.g., aluminum (Al), steel, iron (Fe), alloys thereof, etc.), any non-metallic material (e.g., plastic, polymeric, etc.), a non-magnetic material, a magnetic material, and/or any combinations thereof. For example, receptacle 210 may comprise a metallic receptacle configured for releasable attachment to an x-ray source. Receptacle 210 may include a hollow interior 212 to allow for collimating of the x-ray radiation from the x-ray source array. In order to attach to connecting arm 220, receptacle 210 may comprise an angled channel 214 disposed along an exterior side surface. Channel 214 may be disposed along an entire length of receptacle 210 and can be correspondingly sized and shaped to receive a raised, inner surface 228 of a longitudinal portion 222 of connecting arm 220.

In some aspects, connecting arm 220 may include any suitable material, for example, any metal or metallic material (e.g., aluminum (Al), steel, iron (Fe), alloys thereof, etc.), any non-metallic material (e.g., plastic, polymeric, etc.), a non-magnetic material, a magnetic material, and/or any combinations thereof. For example, connecting arm 220 may comprise a magnetic longitudinal portion 222, elbow 224, and x-ray detector holder 226. A first end of elbow 224 can be disposed towards one end of longitudinal portion 222 and can extend perpendicularly from the longitudinal portion; thereby forming a right angle with the longitudinal portion. X-ray detector holder 226 can be disposed at a second end of elbow 224 and can be configured to fixedly hold an x-ray detector (e.g., 120). Where the x-ray detector is an intraoral x-ray detector, x-ray detector holder 226 can be configured to fixedly position the intraoral x-ray detector within a mouth of a patient.

Longitudinal portion 222 of connecting arm 220 can comprise a raised, inner surface 228 that can be sized and shaped to be removably received in channel 214 of receptacle 210. In some aspects, connecting arm 220 can be configured to be moved into attachment with receptacle 210 and out of attachment with receptacle 210 via magnetic attachment. For example, the magnetic attachment can comprise metal contacts 216 provided along a length of one or both of channel 214 and raised, inner surface 228 of longitudinal portion 222. Metal contacts 216 can be configured to provide immediate feedback on the accuracy of the alignment and connection between channel 214 and inner surface 228. Additionally, such contacts 216 can enable quick release functionality of device 220, which may be useful, for instance, where a patient suddenly moves.

Figure 3A:
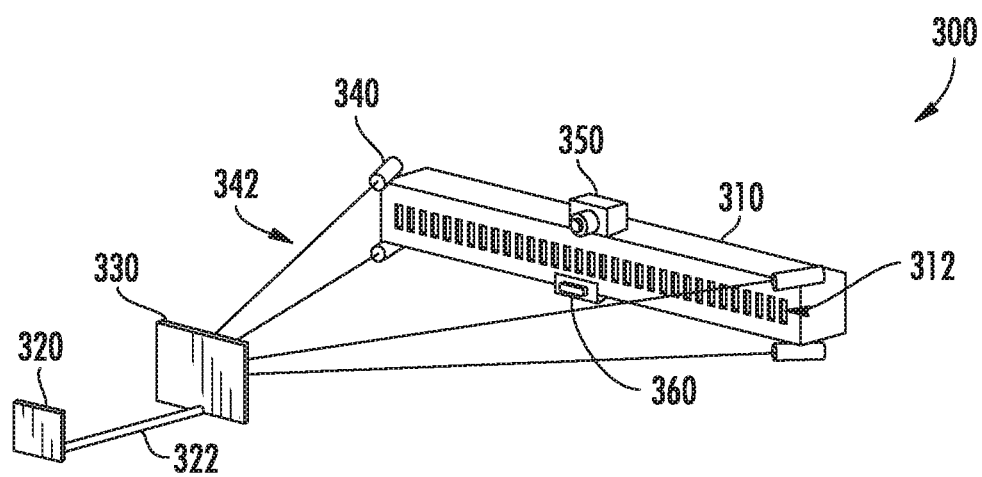
FIG. 3A is a front perspective view illustrating an exemplary geometry calibration device for a digital tomosynthesis system according to some embodiments of the present subject matter.
Figure 3B:
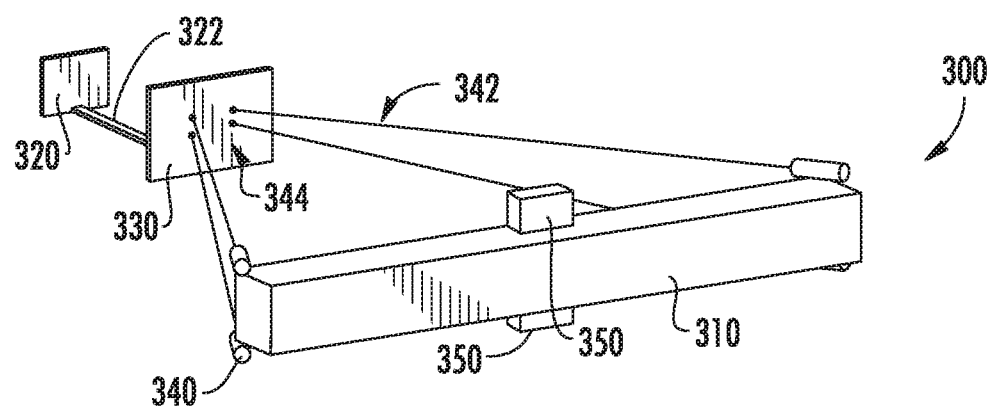
FIG. 3B is a rear perspective view illustrating the exemplary geometry calibration device of FIG. 3A.

Now referring to FIGS. 3A-3B, a first embodiment of an exemplary geometry calibration device 300 for use in an intraoral tomosynthesis system comprising an x-ray source 310 and an x-ray detector 320 is illustrated. Geometry calibration device 300 can comprise, for example, and without limitation a plate or screen 330, at least one light source 340, a camera 350, and at least one gyroscope 360 or any other device for calculating orientation and rotation.

In some aspects, a position of x-ray detector 320 relative to x-ray source 310 may be fixed, although x-ray source 310 and x-ray detector 320 may not be physically connected to one another. For example, x-ray source 310 and x-ray detector 320 may not be physically separated by a mechanical linkage (e.g., 150, FIGS. 2A-2B) where the linkage maintains a fixed position of the x-ray source to the x-ray detector. Rather, x-ray source 310 and x-ray detector 320 may be physically separated from one another such that a relative position of x-ray detector 320 relative to x-ray focal spots of x-ray source 310 may be dynamically determined through geometry calibration techniques, as described in more detail below, in order to determine exact positions of focal spots with respect to x-ray detector 320, which may be advantageous for determining tomosynthesis reconstruction based on 2D projection images. In some aspects, x-ray source 310 may be translated with respect to an object to be imaged. The translation may allow for acquisition of different angular projection images with a single x-ray focal spot or an array of x-ray focal spots. X-ray source 310 can either be translated and stopped at each acquisition location (i.e., step-and-shoot) or can be translated continuously during image acquisition (i.e., continuous motion). Using the calculated locations of the x-ray source during image acquisition, tomosynthesis reconstruction images can be created of the imaged object.

In some aspects, referring to FIG. 3A, x-ray source 310 may comprise an x-ray source array including individually programmable x-ray pixels, generally designated 312. As illustrated in FIG. 3A, 5 to 20 pixels 312 may be distributed as a linear array and may be configured to project onto x-ray detector 320 thereby generating a projection image of an ROI of an object (e.g., teeth of a patient). However, since x-ray source 310 and x-ray detector 320 are not physically connected to one another, geometry calibration device 300 may be utilized to geometrically calibrate a position of x-ray detector 320 relative to x-ray source 310.

In some aspects, at least one light source 340 may project light beams 342 onto plate 330 and produce light spots 344 in order to determine a translational position of plate 330 relative to x-ray source 310. In some aspects, x-ray detector 320 may be physically connected to plate 330. For example, a crossbar 322 may be used to fix x-ray detector 320 to plate 330. Crossbar 322 may comprise a length approximately between 2 cm and 20 cm. In some aspects, crossbar 322 may be adjustable in length. Plate 330 may be composed of paper, plastic, metal or combination of materials with dimensions approximately between 5 cm and 20 cm. In some aspects, crossbar 322 may fix plate 330 to x-ray detector 320 such that plate 330 is in a plane parallel to a plane in which x-ray detector 320 is in. In other aspects, plate 330 may be tilted relative to x-ray detector 320.

In some aspects, where detector 320 is configured as an intraoral x-ray detector, plate 330 may protrude from a mouth of a patient. Thus, through determination of an angular and translational position of plate 330 relative to x-ray source 310, a position of x-ray detector 320 relative to x-ray source 310 may be determined, since plate 330 may be connected at a known and fixed distance to x-ray detector 320.

In some aspects, at least one light source 340 may project onto plate 330. For example, at least one light source 340 may comprise a low-power laser or other light that is configured to project onto plate 330, for example, a 5 mW laser pointer with a 650 nm wavelength. At least one light source 340 may be mounted or otherwise attached to x-ray source 310 and/or a collimator. As illustrated in FIGS. 3A-3B, there may be four light sources 340, each one being positioned at a separate corner of x-ray source 310. Each of the four light sources 340 may be angled towards plate 330 in order to project light beams 342 onto plate 330 and thereby produce four separate light spots 344 (see, e.g., 344A-D, FIG. 4). Depending on an incident angle at which each of the four lights sources 340 are pointed towards plate 330, light spots 344 may form a rectangular, square, triangle, or any other shape with each projected light beam 342 producing light spot 344 forming a corner vertex of the shape. In some aspects, an incident angle at which each light source 340 is mounted onto x-ray source 310 may be known and may be used to determine a translational position of plate 330 relative to x-ray source 310. Notably, positioning at least one light source 340 in this manner may result in the shape formed by light spots 344 produced from projected light beams 342 on plate 330 becoming smaller as plate 330 is moved farther away from x-ray source 310 and becoming larger as plate 330 is moved closer to x-ray source 310.

In some aspects, a camera 350 may record a position of the projected light spots 344 on plate 330 in order to determine the translational position of plate 330 relative to x-ray source 310. In some aspects, camera 350 can also be configured to provide motion tracking and correction during the imaging procedure where there is unintentional movement of the object or system. Camera 350 may comprise a high resolution, high speed digital camera that can be mounted in a known position, for example, on x-ray source 310 or collimator. As illustrated in FIGS. 3A-3B, camera 350 may be centrally mounted on a top surface of x-ray source 310 and adjacent to a front surface edge of x-ray source 310. In some aspects, camera 350 may transmit captured photographic images to a computing platform (see, e.g., 804, FIG. 8). For example, camera 350 may transmit photographic images capturing a position of light spots 344 on plate 330 to the computing platform in order to determine a translational position of plate 330 relative to x-ray source 310; and thereby determining a position of x-ray detector 310 relative to x-ray source 310.

In some aspects, at least one gyroscope 360 may be configured to determine an angular position of plate 330 relative to x-ray source 310. For example, at least one gyroscope 360 may include a Parallax Gyroscope Module 3-Axis L3G4200D, which commercially available from manufacturers including, for example, Parallax Inc. Accordingly, determining an angular position of plate 330 relative to x-ray source 310 can be achieved in one of several techniques. For example, a first technique may comprise mounting a first gyroscope 360 at x-ray source 310 and a second gyroscope (not shown) at plate 330 and comparing the data points from each gyroscope at a computing platform. In another example, a second technique may comprise resetting plate 330 by positioning plate 330 in a same plane as x-ray source array 310, resetting data of a first gyroscope 360 mounted at x-ray source 310, and measuring a deviation from the initial x-ray source plane during the imaging process.

Figure 4:
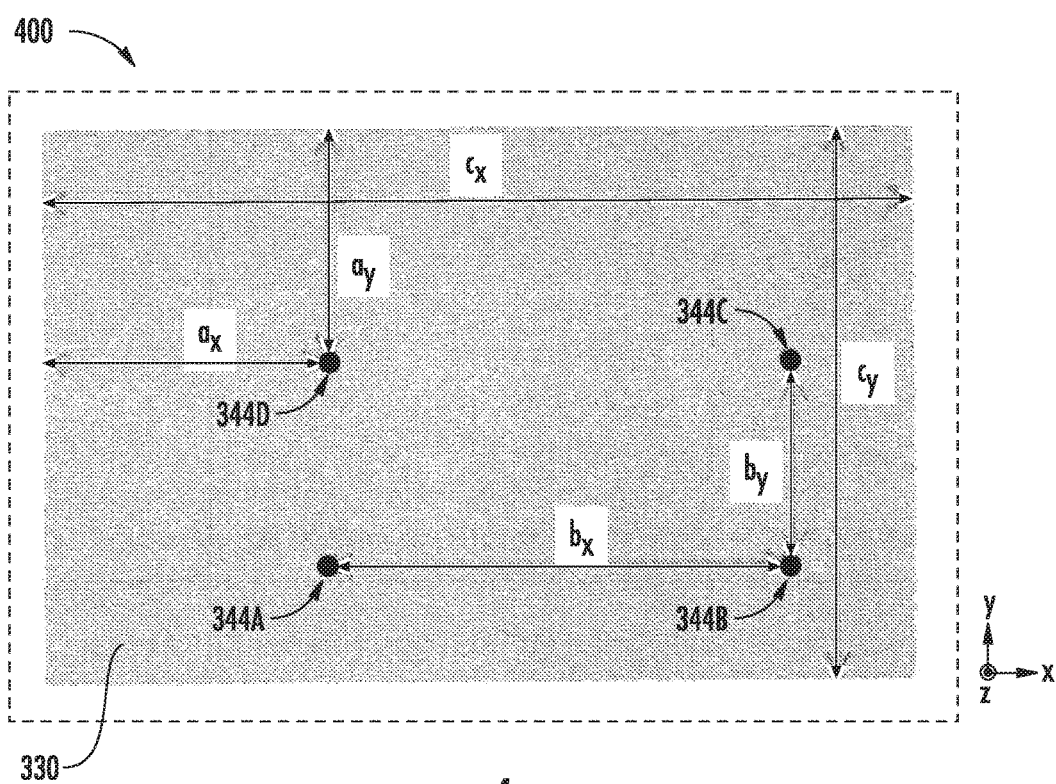
FIG. 4 is a screen capture illustrating a process for determining tomosynthesis imaging geometry using the exemplary geometry calibration device of FIGS. 3A-3B.

Referring now to FIG. 4, an exemplary screen capture from a camera (e.g., 350) illustrates the captured image resulting from light beams 342 projecting onto plate 330 and producing light spots 344A-D. In this example, four separate light spots 344A-D are produced from light beams 342 generated from four separate light sources 340 arranged in a similar manner to that described above in reference to FIGS. 3A-3B, where each light spot 344A-D forms one corner or vertex of a rectangular shape. A coordinate system can be defined to establish x, y, and z directions for determining a translational position of x-ray detector 320 relative to x-ray source 310. In some aspects, a distance between each light spot can determine a z-offset of plate 330 relative to x-ray source 310. For example, a horizontal or x-distance $b_x$ measured between a first light spot 344A and a second light spot 344B or a vertical or y-distance $b_y$ measured between second light spot 344B and third light spot 344C can determine a z-offset of plate 330, and thus, of x-ray detector 320, relative to x-ray source 310 because the distance between spots 344A-D are uniquely determined by a specification of any diffraction grating attached to at least one light source 340, a wavelength of at least one light source 340, and the z-offset. In other aspects, a ratio of a distance from a light spot to an edge of plate 330 to distance between opposing edges of plate 330 can determine an x-offset or a y-offset of plate 330 relative to x-ray source 310. For example, a ratio of a horizontal or x-distance $a_x$ from light spot 344D to an edge of plate 330 to a horizontal or x-distance $c_x$ between two opposing edges of plate 330 (i.e., $a_x/c_x$) can determine an x-offset of plate 330, and thus, x-ray detector 320, relative to x-ray source 310. In another example, a ratio of a vertical or y-distance $a_y$ from light spot 344D to an edge of plate 330 to a vertical or y-distance $c_y$ between two opposing edges of plate 330 (i.e., $a_y/c_y$) can determine a y-offset of plate 330, and thus, x-ray detector 320, relative to x-ray source 310.

Figure 5A:
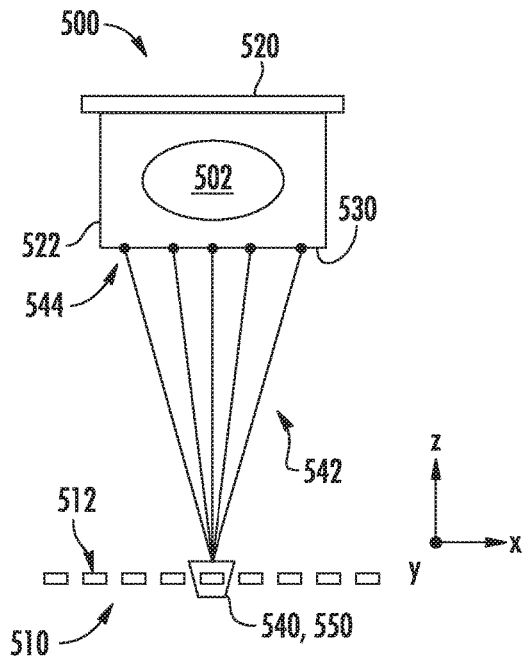
FIGS. 5A-5D are schematic views illustrating an exemplary geometry calibration device for an intraoral tomosynthesis system according to some embodiments of the present subject matter.
Figure 5B:
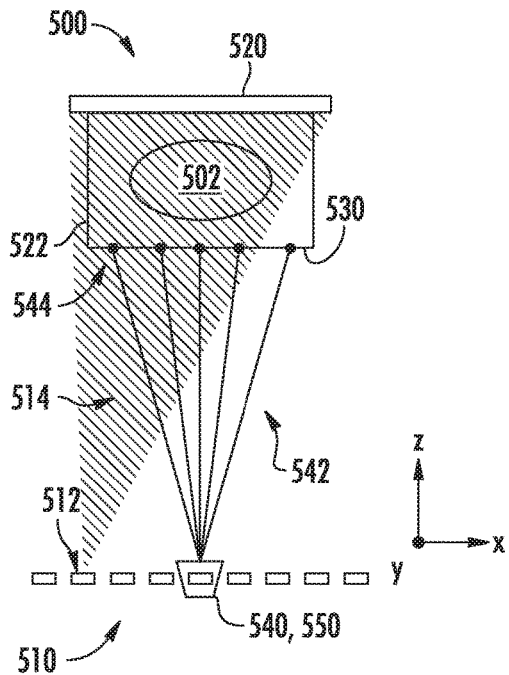
Figure 5C:
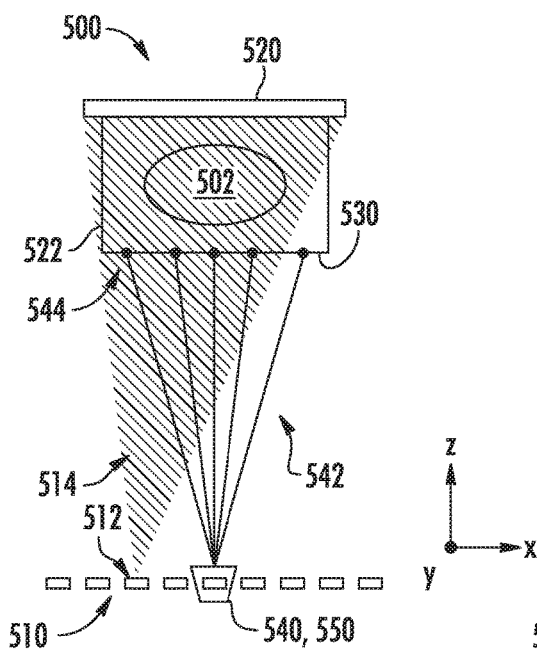
Figure 5D:
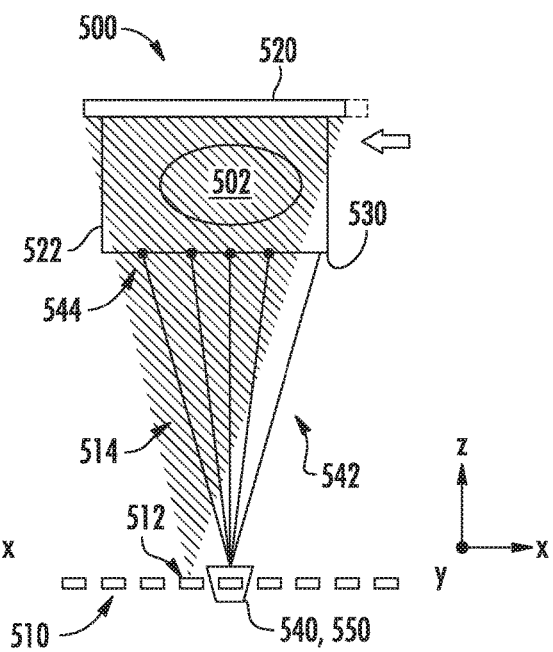

Referring now to FIGS. 5A-5D and 6A-6C, a second embodiment of an exemplary geometry calibration device 500 for use in an intraoral tomosynthesis system comprising an x-ray source 510 and an x-ray detector 520 is illustrated. FIGS. 5A-5D illustrate exemplary sequential acquisition of tomography images using a geometry calibration device 500. Where FIG. 5A illustrates an initial set-up of geometry calibration device 500, FIGS. 5B-5D illustrate sequential activation of different cathodes in an array of an x-ray source at two different positions (e.g., a first position illustrated in FIGS. 5B-5C and a second position illustrated in FIG. 5D). Notably, device 500 can comprise, for example, and without limitation, a plate or screen 530, a light source 540, and a camera 550.

Referring to FIG. 5A, device 500 can be configured in an initial configuration prior to acquisition of 2D projection images. Although a position of x-ray detector 520 relative to x-ray source 510 may be fixed, x-ray source 510 and x-ray detector 520 may not be physically connected to one another. For example, x-ray source 510 and x-ray detector 520 may not be physically separated by a mechanical linkage where the linkage maintains a fixed position of the x-ray source to the x-ray detector. (e.g., 150, FIGS. 2A-2B). Rather, x-ray source 510 and x-ray detector 520 may be physically separated from one another such that a relative position of x-ray detector 520 relative to x-ray source 510 may be dynamically determined through geometry calibration techniques, as described in more detail below.

In some aspects, x-ray source 510 may comprise an x-ray source array including individually programmable x-ray pixels, generally designated 512. As illustrated in FIGS. 5A-5D, nine pixels 512 may be distributed as a linear array and may be configured to be individually activated in order to sequentially project x-ray beams 514 (see, e.g., FIGS. 5B-5D) onto x-ray detector 520 in order to generate a projection image of an ROI of an object 502 (e.g., teeth of a patient). However, since x-ray source 510 and x-ray detector 520 are not physically connected to one another, geometry calibration device 500 may be utilized to geometrically calibrate a position of x-ray detector 520 relative to x-ray source 510.

In some aspects, x-ray detector 520 may be physically connected to plate 530. For example, a crossbar 522 may be used to fix x-ray detector 520 to plate 530. Crossbar 522 may comprise a length approximately between 2 cm and 20 cm. In some aspects, crossbar 522 may be adjustable in length. Plate 530 may be composed of paper, plastic, metal, or the combination of thereof. In some aspects, crossbar 522 may fix plate 530 to x-ray detector 520 such that plate 530 is in a plane parallel to a plane in which x-ray detector 520 is in. In other aspects, plate 530 may be tilted relative to x-ray detector 520.

In some aspects, where detector 520 is configured as an intraoral x-ray detector, plate 530 may protrude from a mouth of a patient. Thus, through determination of an angular and translational position of plate 530 relative to x-ray source 510, a position of x-ray detector 520 relative to x-ray source 510 may be determined, since plate 530 may be connected at a known and fixed distance to x-ray detector 520 (e.g., using crossbar 522). Plate 530 may be composed of paper, plastic, metal or combination of materials with dimensions approximately between 5 cm and 20 cm.

A light source 540 may be configured to project light beams 542 onto plate 530 and produce light spots 544 in order to determine a translational position of plate 530 relative to x-ray source 510. In some aspects, only one light source 540 may be needed, in comparison with the first embodiment of geometry calibration device 300. Light source 540 may be mounted or otherwise attached to x-ray source 510 and/or a collimator. In some aspects, light source 540 is integral with a camera 550, both of which may be configured to be attached to source 510. As illustrated in FIGS. 5A-5D, light source 540 may be mounted with a camera 550 and centrally mounted on x-ray source 510 and adjacent to a front surface edge thereof. Notably, light source 540 may comprise a low-power laser or other light that is configured to project onto plate 530, for example, a 5 mW laser pointer with a 650 nm wavelength.

In some aspects, at least one diffraction grating (not shown) with a known diffraction line spacing can be attached to x-ray source 510 at a known relative position. For example, one dimensional (1D) diffraction grating can be used. In another example, two gratings can be used where a first grating is a 1D diffraction grating and a second grating is a 2D diffraction grating. In some aspects, the gratings can each comprise a diffraction line spacing that can be similar to or different than one another. The diffraction line spacing can comprise a distance between each diffraction line in the grid. In other aspects, gratings can comprise a same optical dimension, and can be oriented in different directions relative to one another. Where geometry calibration device 500 comprises at least one diffraction grating, light source 540 can be mounted such that light beam 542 pass through the diffraction grating(s) at a known location relative to x-ray source 510, where passing through the gratings results in light source 540 being separated according to the following separation equation:

$$y = \frac{m\lambda D}{d},$$

in the vertical (y) and horizontal (x) directions, where m=0, 1, 2, 3, . . . indicates an order of diffraction spot, $\lambda$ is the wavelength of light source 540, D is the distance of plate 530 from the diffraction origin, and d is the diffraction grating slit separation.

In some aspects, a camera 550 may record a position of the projected light spots 544 on plate 530 in order to determine the translational position of plate 530 relative to x-ray source 510. In some aspects, camera 550 can also be configured to provide motion tracking and correction during the imaging procedure where there is unintentional movement of object 502 or system (e.g., system 100). Camera 550 may comprise a high resolution, high speed digital camera that can be mounted in a known position, for example, on x-ray source 510 or collimator. As discussed above, camera 550, as well as light source 540, may be centrally mounted on x-ray source 510 and adjacent to a front surface edge of x-ray source 510. In some aspects, camera 550 may transmit captured photographic images to a computing platform (see, e.g., 804, FIG. 8). For example, camera 550 may transmit photographic images capturing a position of light spots 544 on plate 530 to the computing platform in order to determine a translational position of plate 530 relative to x-ray source 510; and thereby determining a position of x-ray detector 510 relative to x-ray source 510.

Accordingly, light source 540, as well as camera 550, may be angled towards plate 530 in order to project light beams 542 through the at least one diffraction grating and onto plate 530 and thereby produce light spots 544 (see, e.g., 544A-C, FIGS. 6A-6C) at different positions on screen 530 and, thus, provide a light pattern on screen 530. Notably, different positions of light source 540 and/or screen 530 can result in different light patterns, which can each be captured by camera 550 and used to calibrate a geometry of screen 530 and attached detector 520 relative to each pixel in x-ray source 510.

Once device 500 is configured and is ready for generation of 2D projection images, camera 550 can be configured to capture an initial light pattern produced by light source 540 (e.g., laser) when x-ray detector 520 and screen 530 are in a first position and transmit the captured pattern to a computing platform (e.g., 1000) for processing and geometry calibration. For example, camera 550 can be configured to capture light spots 544 forming an initial light pattern on screen 530 when x-ray detector 520 and screen 530 are in an initial or first position. Processing of this captured image can be used as a reference for geometry calibration purposes.

Now referring to FIGS. 5B-5D, acquisition of 2D projection images is illustrated, where each pixel 512 in the source array of x-ray source 510 is sequentially activated when x-ray detector 520 and screen 530 are in a first position and a second position. Activation may be accomplished by control electronics (e.g., controller 130, FIG. 1), which may be configured to regulate x-ray radiation and synchronization of the x-ray radiation with detector 530, such that multiple two dimensional (2D) projection images of an ROI of an object can be acquired. Although FIGS. 5B-5D illustrate sequential activation of only three cathodes and only two different positions, one of skill in the art may recognize that these are only for illustration purposes. For example, each pixel 512 in x-ray source 510 can be activated and detector 520 can record the image. As illustrated in FIGS. 5A-5D, where there are nine cathodes 512, all nine can be individually activated and x-ray detector 520 can be configured to record each image for each position of x-ray detector 520. In some aspects, x-ray detector 520 need only be in one position, in which case the nine cathodes need only be activated once, individually. However, if x-ray detector 520 is moved into multiple positions, each of the nine cathodes may also be reactivated individually when x-ray detector 520 is in subsequent positions.

Initially, prior to the acquisition of 2D projection images illustrated in FIGS. 5B-5D, it may be noted that x-ray detector 520 may first be disposed relative to a ROI. For example, an area digital x-ray detector 520 may be inserted inside a mouth of a patient (not shown). Further, a connectable geometry calibration mechanism can be connectably attached to area digital x-ray detector 520. In some aspects, the geometry calibration mechanism may comprise a screen or plate (e.g., screen 530, FIGS. 5A-5D) fixedly attached to the area digital x-ray detector by a mechanical linkage (e.g., cross bar 522, FIGS. 5A-5D) and located outside the mouth of the patient between x-ray source array 510 and the area digital x-ray detector 520. In alternative embodiments, the geometry calibration mechanism may comprise a magnetic attachment attachable to the area digital x-ray detector while the detector is inside the mouth of the patient (see, FIG. 2B).

Additionally, x-ray source array 510 can be positioned relative to the object. For example, x-ray source array 510 can be positioned outside the mouth of the patient. Where the geometry calibration mechanism comprises a screen (e.g., screen 530, FIGS. 5A-5D), x-ray source array 510 can be positioned such that a laser array (e.g., 540, FIGS. 5A-5D) may be aimed onto screen (e.g., screen 530, FIGS. 5A-5D) of the geometry calibration mechanism.

In FIG. 5B, a second pixel 512 in x-ray source 510 can be activated in order to generate an x-ray beam 514 that projects onto detector 520, which records the projected image, when screen 530 and attached x-ray detector 520 are in a first position. Notably, prior to the second pixel 512 in x-ray source 510 being activated, a first pixel in x-ray source 510 may have been activated and x-ray detector 520 may have recorded the image. Likewise, in FIG. 5C, a third pixel 512 in x-ray source 510 can be activated in order to generate an x-ray beam 514 that projects onto detector 520, which records the projected image, when screen 530 and attached x-ray detector 520 are in a first position. Since screen 530 remains in the first position during activation of the second pixel 512 and the third pixel in array 512, the light pattern produced by light spots 544 will remain the same for geometry calibration purposes.

In FIG. 5D, however, screen 530 and x-ray detector 520 can be moved into a second position, which is different than the first position. For example, screen 530 and x-ray detector 520 can be moved in an x-direction towards the left relative to x-ray source 510. Although screen 530 and x-ray detector 520 can be moved, x-ray source 510 can remain in its initial position. In such a scenario, when light beams 542 project onto screen 530, a light pattern formed from light spots 544 will comprise a different geometry since light spots 544 project onto screen 530 at a different location than when screen 530 was in the first position. This remains true for any subsequent position in which screen 530 and attached x-ray detector are moved into, where each subsequent position differs from the first position.

Accordingly, once screen 530 and x-ray detector 520 are moved into the second (or any position different than the first position), camera 550 can be configured to capture a second light pattern produced by light source 540 (e.g., laser) when x-ray detector 520 and screen 530 are in the second position (or any position different than the first position) and transmit the captured pattern to a computing platform (e.g., 1000) for processing and geometry calibration. For example, camera 550 can be configured to capture light spots 544 forming a second light pattern on screen 530 when x-ray detector 520 and screen 530 are in a second position. Processing of this captured image can be used as a reference for geometry calibration purposes. In some aspects, and still referring to FIG. 5D, a fourth pixel 512 in x-ray source 510 can be activated in order to generate an x-ray beam 514 that projects onto detector 520, which records the projected image, when screen 530 and attached x-ray detector 520 are in the second position. Activation of each successive pixel 512 in x-ray source 510 at the second position can also occur, In some aspects, once each pixel 512 in x-ray source 510 has been activated and the projected image recorded by x-ray detector 520, 3D image reconstruction can be initiated. For example, 3D image reconstruction can comprise tomosynthesis reconstruction. 3D image reconstruction can be accomplished using a computer program and/or workstation (e.g., 1000, FIG. 10) to analyze, calibrate, reconstruct, display, etc., 3D tomographic images from the recorded 2D projection images. The geometry calibration data (e.g., photographic images) captured and recorded by camera 550 can be utilized by the computer program and/or workstation to determine the relative position of each pixel 512 of the x-ray source 510 with respect to the detector, these position parameters are then used for tomosynthesis reconstruction of the 3D images of the teeth.

Referring now to FIGS. 6A-6C, FIGS. 6A-6C each illustrate a captured image resulting from light beams 542 projecting onto plate 530 and producing light spots 544. Each of FIGS. 6A-6C illustrates a different position and/or orientation of screen 530 relative to a light source (e.g., 540). Notably, moving screen 530 relative to the light source can result in the light pattern produced by light spots 544 on screen 530 changing. Thus, by comparing and analyzing a pattern of light spots 544, a relative movement of x-ray source 510 relative to detector 520 can be determined.

For example, FIG. 6A illustrates a first schematic 600A of a first position and first orientation of screen 530A relative to a light source. In FIG. 6A, light spots 544A form a first light pattern indicative of screen 530 being positioned in a plane parallel to a plane containing the light source, which is mounted on an x-ray source (e.g., 510), and screen 530A being positioned at a 'short z-distance' relative to the light source. Here, "short" is defined relative to FIG. 6B and a "long z-distance", as screen 530A is positioned a smaller z-distance from the x-ray source than when it is positioned a long z-distance. Accordingly, the closer that screen 530A is positioned in a z-direction to the light source, the more closely spaced light spots 544A of the light pattern will be.

In another example, FIG. 6B illustrates a second schematic 600B of a second position still at a first orientation of screen 530B relative to a light source. In FIG. 6B, light spots 544B form a second light pattern indicative of screen 530B being positioned in a plane parallel to a plane containing the light source, which is mounted on an x-ray source, and screen 530B being positioned at a 'long z-distance' relative to the light source. Accordingly, the farther that screen 530B is positioned in a z-direction to the light source, the more spread apart light spots 544B of the light pattern will be.

In a further example, FIG. 6C illustrates a third schematic 600C of a third position and a second orientation of screen 530C relative to a light source. In FIG. 6C, light spots 544C form a third light pattern indicative of screen 530C being positioned in a plane rotated relative to a plane containing the light source, which is mounted on an x-ray source, and screen 530C being positioned at approximately between a 10 cm to a 40 cm z-distance relative to the light source. Where screen 530C is rotated relative to a plane containing the light source, relative distances between each light spot 544C may be different than when screen 530C is parallel to the plane containing the light source. In such a case, a rotation calculation may be used during calibration in order to determine an angular position of an x-ray detector (e.g., 520) connected with screen 530C relative to an x-ray source. Accordingly, the more that screen 530C is rotated relative to the plane containing the light source, the more that the relative distances between each light spot 544C of the light pattern will increase. Conversely, the less that screen 530C is rotated relative to the plane containing the light source, the less that the relative distances between each light spot 544C of the light pattern will increase.

Figure 7:
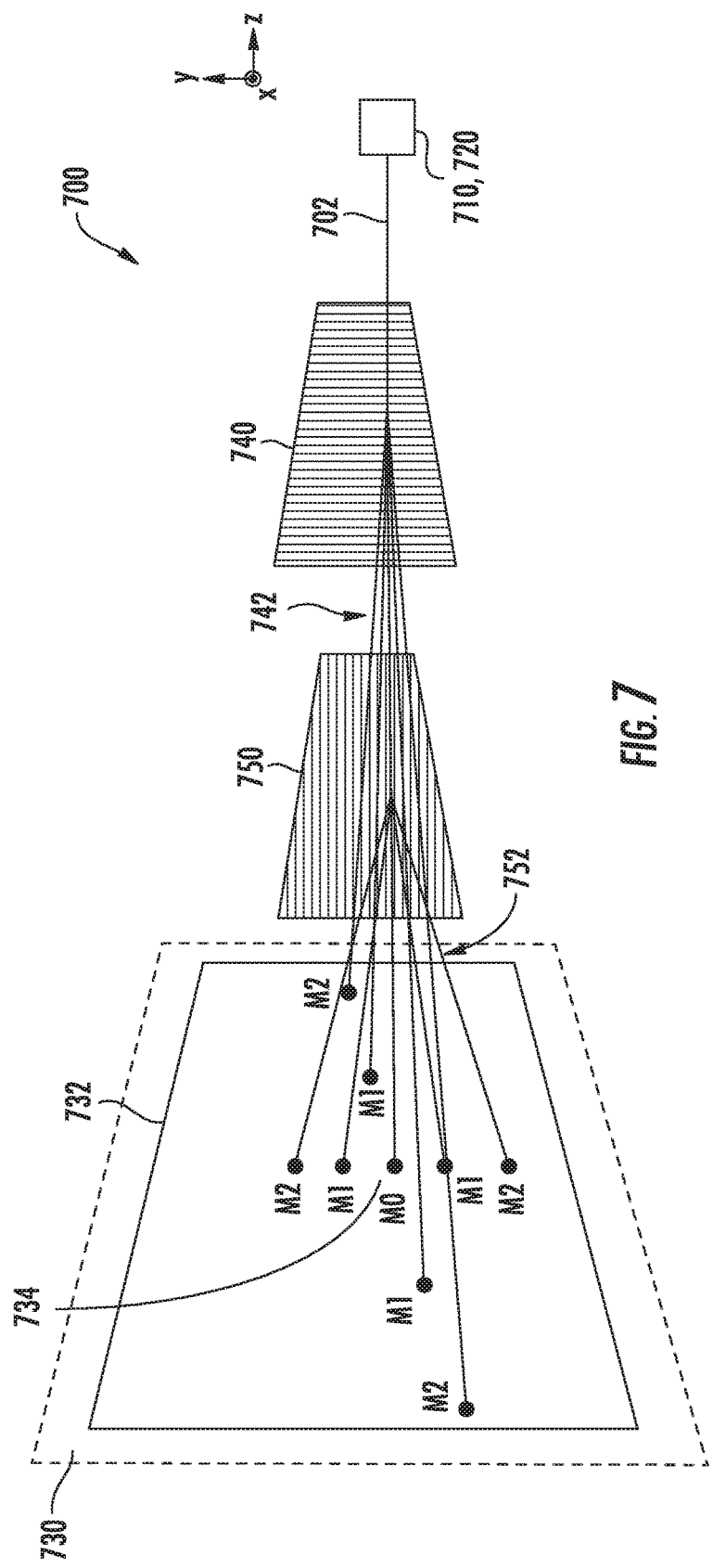
FIG. 7 is a schematic view illustrating an exemplary geometry calibration device for a digital tomosynthesis system according to some embodiments of the present subject matter.

Referring now to FIG. 7, a third embodiment of an exemplary geometry calibration device 700 for use in an intraoral tomosynthesis system, e.g., system 100, is illustrated. Geometry calibration device 700 can comprise, for example, and without limitation, a light source 710, a camera 720, a screen or plate 730, a first grating 740, and a second grating 750.

Light source 710 can comprise a visible light laser or any other light source attached to the x-ray source array (not shown in this embodiment). Light source 710 can comprise a known (i.e., pre-determined) frequency and wavelength. In some aspects, only one light source 710 may be needed, in comparison with the first embodiment of geometry calibration device (e.g., 300). In some aspects, a camera 720 may be mounted relative to light source 710 and attached to the x-ray source array for capturing an image of visible light diffraction spots M1-M4 projected onto screen 730. For example, camera 720 can be mounted either above or below light source 710.

In some aspects, light source 710 can project onto screen or plate 730 through at least one optical diffraction grating. In the embodiment of the geometry calibration device illustrated in FIG. 7, there can be two optical diffraction gratings 740 and 750. Screen or plate 730 can be attached to an x-ray detector (not shown in this embodiment) at a known relative position and positioned in front of a ROI of an object to be imaged. For example, screen 730 can be attached to an intraoral x-ray detector and positioned outside a mouth of a patient. Plate 730 can be attached to the x-ray detector at a known and relative position, using, for example, a crossbar (e.g., 322, 522 FIGS. 3A-3B and 5A-5D). Plate 730 may be composed of paper, plastic, metal or combination of materials with dimensions approximately between 5 cm and 20 cm.

In some aspects, plate 730 can comprise a predetermined calibrated marker 732 either centered or otherwise. Predetermined calibrated marker 732 can comprise a square or other enclosed shape encompassing an area within. Light source 710 may be configured to project a split light beam 752 onto plate 730, in particular, within the shape formed by calibrated marker 732. Predetermined calibrated marker 732 can be used as a reference point relative to light spots M0, M1, M2, etc., in order to determine a position of an x-ray detector to which plate 730 is attached relative to an x-ray source, which will be discussed in more detail below. In some aspects, plate 730 can comprise a calibration circle 734 defined within the predetermined calibrated marker 732. A position of calibration circle 734 can be predetermined by an operator as corresponding to a desired position of light source 710. Thus, an operator can adjust a position of light source 710 so that a light beam 702 generated by light source 710 produces an initial light spot M0 within calibration circle 734.

In some aspects, at least one diffraction grating can be attached to an x-ray source at a known position. As illustrated in FIG. 7, two diffraction gratings 740 and 750 can be positioned in front of light source 710, such that light beams emitted from light source 710 can project through gratings 740 and 750, which can split the light beam. The split light beam can then project onto plate 730 in the form of multiple light spots M1, M2. Notably, initial light spot M0 from the light beam can also be projected onto plate 730.

In some aspects, grating 740 and 750 can be either 1D or 2D optical diffraction gratings with a known diffraction line spacing therebetween. For example, a first grating 740 is a 1D diffraction grating and a second grating 750 is a 2D diffraction grating. In some aspects, gratings 740 and 750 can each comprise a diffraction line spacing that can be similar to or different than one another. The diffraction line spacing can comprise a distance between each diffraction line in the grid. For example, first diffraction grating 740 and/or second diffraction grating 750 can be configured with a diffraction line spacing that can comprise diffraction lines spaced apart, for example, from approximately between 0.001 mm to 0.1 mm. In other aspects, gratings 740 and 750 can comprise a same optical dimension, and can be oriented in different directions relative to one another. In FIG. 7, for example, first diffraction grating 740 and second diffraction grating 750 can be rotationally oriented relative to one another. For example, an orientation of first grating 740 can be rotated 90 degrees relative to an orientation of a second grating 750.

Gratings 740 and 750 can be configured to split an initial light beam 702 emitted by light source 710 in order to generate multiple light spots M1, M2 on plate 730. Initial light beam 702 can be a light beam comprising a wavelength in the visible range (i.e., from approximately 390 nm to 700 nm). Initial light spot M0 can be produced by light beam 702 and can be used as a reference for positioning light source 710, and thereby the x-ray source, within calibration circle 734. In some aspects, gratings 740 and 750 can be attached to an x-ray source array at a known relative position.

Light beam 702 can also be configured to pass through one or more diffraction gratings. Where geometry calibration device 700 comprises at least one diffraction grating (e.g., gratings 740 and 750), light source 710 can be mounted such that light beam 702 passes through diffraction gratings 740, 750 at a known location relative to an x-ray source, where passing through gratings 740, 750 results in light source 710 being separated according to the following separation equation:

$$y = \frac{m\lambda D}{d},$$

in the vertical (y) and horizontal (x) directions, where m=0, 1, 2, 3, . . . indicates an order of diffraction spot, $\lambda$ is the wavelength of light source 540, D is the distance of plate 530 from the diffraction origin, and d is the diffraction grating slit separation. As illustrated in FIG. 7, for example, light beam 702 can pass through first diffraction grating 740 and second diffraction grating 750, each being rotated 90 degrees relative to one another. First diffraction grating 740 can be configured with a second diffraction line spacing that can comprise vertical lines spaced apart, for example, from approximately between 0.001 mm to 0.1 mm, while second diffraction grating 750 can be configured with a second diffraction line spacing that can comprise horizontal lines spaced apart, for example, from approximately between 0.001 mm to 0.1 mm. Beam 702 can, thus, be split by first diffraction grating 740 into multiple beams 742, which can each pass through second diffraction grating 750. For example, beam 702 can be split into separate beams, while beams 742 can be split into separate beams 752. In some aspects, split beams 752 can project onto plate 730 within an area defined by predetermined calibrated marker 732. For example, eight separate beams 752 can project onto plate 730 and form a 2D light pattern comprising eight separate light spots M1, M2. In this example, four light spots M1 and four light spots M2 can be formed, with initial light spot M0 being positioned within a center of the light pattern formed from light spots M1, M2. However, multiple orders of diffraction spots, such as M0, M1, M2, can be used to determine a position of at least one light source 710 relative to plate 730, and thus, the position of the x-ray source relative to the x-ray detector.

Figure 8:
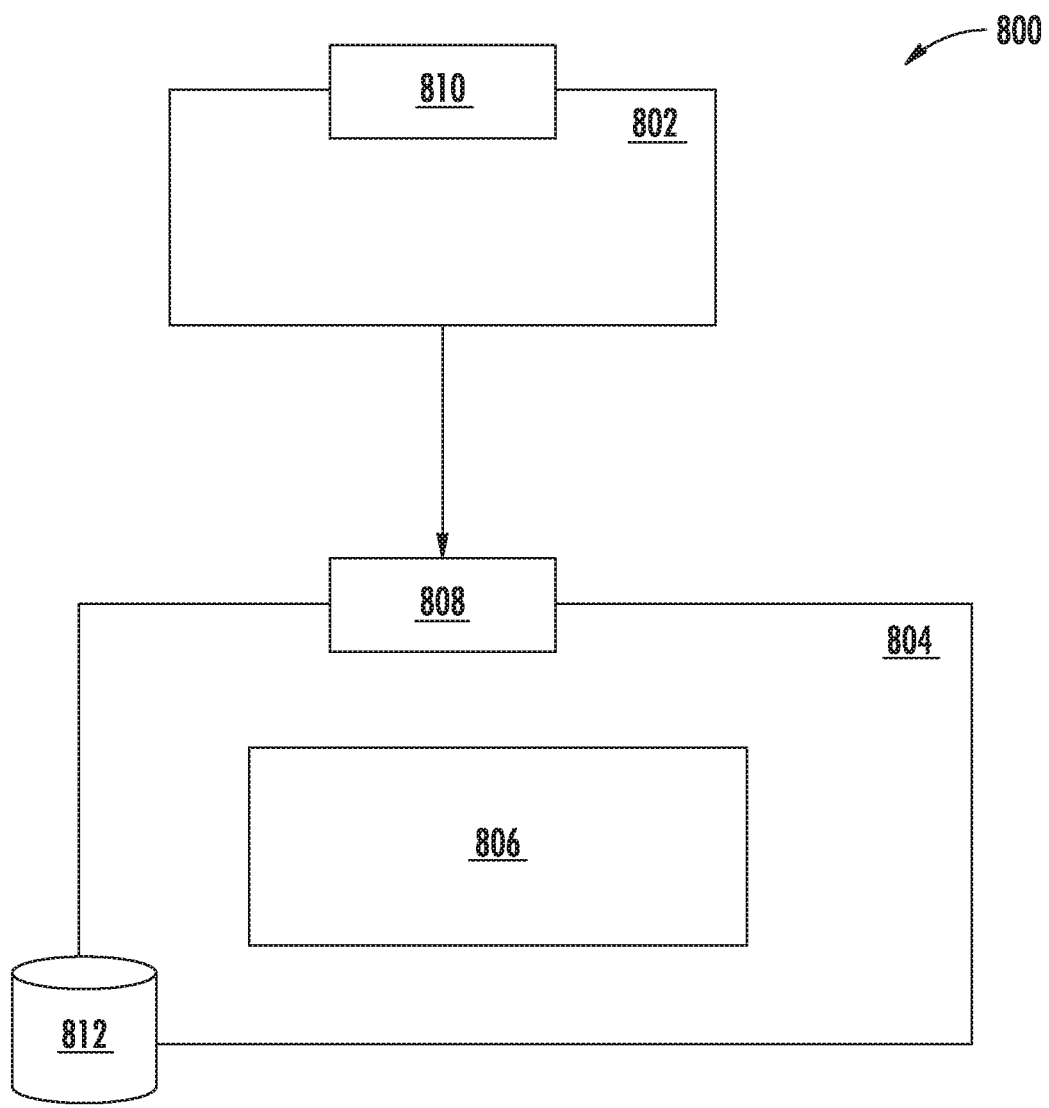
FIG. 8 is a system diagram illustrating an exemplary digital tomosynthesis system interfacing with an exemplary computing platform according to some embodiments of the present subject matter.

In some aspects, camera 720 can be configured to capture at least one projection image of light spots M1, M2, and initial light spot M0 within predetermined calibration marker 732 and transmit the at least one captured image to a computing platform (see, e.g., 804, FIG. 8). For example, camera 720 may transmit images capturing a position of initial light spot M0 and light spots M1, M2 within calibration marker 732 on plate 730 to the computing platform for determining a translational position of plate 730 relative to the x-ray source and thereby determining a position of the x-ray detector relative to the x-ray source. Accordingly, using the light pattern comprised of initial light spot M0, light spots M1, M2, predetermined calibration marker 732, and diffraction angle $\theta_m$ for each intensity peak, a distance between a position when the laser hits first grating 740 and each light spot M1, M2 on the plate 730 can be determined at the computing platform. For example, a geometry calibration module can calculate a distance between a position when the laser hits first grating 740 and each light spot M1, M2 on the plate 730, as well as three angles of axial rotation of the plate 730. Notably, all six degrees of freedom of plate 730 can be determined from the light pattern formed by light spots M1, M2 relative to a point of the first beam split (i.e., a position when the laser hits first grating 740). Consequently, a full geometry of the imaging system can be determined based on a relative position of the x-ray detector to plate 730 and an x-ray source relative to light source 710.

Accordingly, regardless of the technique used for geometry calibration purposes, an angular and/or translational position of an x-ray detector relative to an x-ray source can be determined, which can aid in accurately reconstructing tomosynthesis images from the acquired x-ray projection images. Thus, the determined positions (e.g., angular position and/or translational) of the x-ray source during image acquisition can enable tomosynthesis reconstruction images to be created of the imaged object.

Referring now to FIG. 8, a system diagram, generally designated as 800, of an exemplary tomosynthesis system, generally designated 802, interfacing with an exemplary computing platform, generally designated 804, is illustrated. Notably, when configured as described herein, exemplary computing platform 804 becomes a special purpose computing platform that can improve the technological field of intraoral tomosynthesis imaging by acquiring 2D projection images from multiple viewpoints and processing such images, without movement of the x-ray source or the patient.

In some aspects, exemplary tomosynthesis system, generally designated 802, can comprise a tomosynthesis system such as the one described above in FIG. 1 (e.g., 100). In some aspects, tomosynthesis system 802 may comprise a geometry calibration device 810, such as the ones described above in (e.g., 300, 500, 700). Tomosynthesis system 802 may be configured to interface with a computing platform 804 for calibrating geometry of system 802 through processing of photographic images. Computing platform 804 may also be configured for tomosynthesis reconstruction of 2D projection images.

Computing platform 804 may be configured to perform one or more aspects associated with calibrating geometry of system 802. In some aspects, computing platform 804 may be a stand-alone entity or entities, a device, or software executing on a processor. In some aspects, computing platform 804 may be a single node or may be distributed across multiple computing platforms or nodes.

In some aspects, computing platform 804 may include a geometry calibration module 806 configured to perform one or more aspects associated with calibrating geometry of system 802. In some aspects, computing platform may also include a separate tomosynthesis reconstruction module (not shown) configured to reconstruct acquired 2D x-ray projection images. Notably, geometry calibration module 806 may be configured to perform tomosynthesis reconstruction, as well as geometry calibration. Geometry calibration module 806 may be any suitable entity (e.g., software executing on a processor) for performing one or more aspects associated with geometry calibration of system 802. Geometry calibration module 806 may include functionality for receiving at least one photographic image from a camera (e.g., 350, 550, 720) during one or more image acquisition session. For example, an interface 808 associated with geometry calibration module 806 and/or computing platform 804 may receive a photographic image of various positions of light spots, light spots etc., on screen, plate, etc., from geometry calibration device 810 for each adjustment in position of an x-ray detector relative to an ROI of an object to which the screen, plate, etc., is attached. In this example, a geometry calibration module user (e.g., a device or computing platform usable by a user or an operator) may capture at least one photographic image of light spots, light spots etc., on screen, plate, etc., for each adjustment in position of the x-ray detector relative to an ROI of an object, which may be subsequently received by geometry calibration module 806.

A tomosynthesis reconstruction module, separate from or integral to geometry calibration module, may be configured to acquire, process, and/or reconstruct 2D x-ray projection images of the object for tomosynthesis reconstruction purposes. For example, a tomosynthesis reconstruction module or software package can be configured to acquire, process, and reconstruct 2D x-ray projection images of the object via a variety of algorithms including, but not limited to, filtered back projection, iterative reconstruction, simultaneous algebraic reconstruction, adapted fan beam volume reconstruction, limited angle tomography reconstruction, or other compressed sensing tomography reconstruction.

Computing platform 804 and/or geometry calibration module 806 may include functionality for storing the one or more photographic images for future use. In some aspects, computing platform 804 and/or geometry calibration module 806 may include functionality for instantiating or initializing images and/or for providing the images to other computing platforms or devices. For example, computing platform 804 and/or geometry calibration module 806 may receive the one or more photographic images, calibrate geometry of system 802 based on those images, and/or provide those images to other nodes, via interface 808, for geometry calibration of system 802.

In some aspects, computing platform 804 and/or geometry calibration module 806 may include or access data storage 812 containing data and/or photographic images related to geometry calibration of system 802. For example, computing platform 804 and/or geometry calibration module 806 may access data storage 812 containing previous photographic image(s), mapped coordinate systems, image data, profiles, settings, or configurations. Exemplary data storage may include non-transitory computer readable media, such as flash memory, random access memory, or other storage devices. In some aspects, data storage may be external to and/or or integrated with computing platform 804 and/or geometry calibration module 806.

In some embodiments, computing platform 804 and/or geometry calibration module 806 may include one or more communications interfaces for interacting with users and/or nodes. For example, computing platform 804 and/or geometry calibration module 806 may provide a communications interface for communicating with a user of computing platform 804 and/or geometry calibration module 806. In some aspects, user of computing platform 804 and/or geometry calibration module 806 may be an automated system or may be controlled or controllable by a human user. User of computing platform 804 and/or geometry calibration module 806 may use the camera of device 810 to capture one or more photographic images and transmit those images to computing platform 804 and/or geometry calibration module 806.

In some embodiments, computing platform 804 may include functionality for configuring system 802, as described herein, for acquiring 2D x-ray projection images of an ROI of an object. For example, computing platform 804 may control acquisition of 2D x-ray projection images using system 802 by initiating an x-ray source to begin generation of x-ray beams. In another aspect, computing platform 802 may include functionality to modify conditions within system 802; for example, moving a translational stage, moving an x-ray detector relative to an object, etc. In some aspects, computing platform 804 may include functionality to generate content (e.g., reconstructed 3D tomosynthesis images using previously acquired 2D x-ray projection images) and/or retrieve stored content associated with an imaging session).

Figure 9:
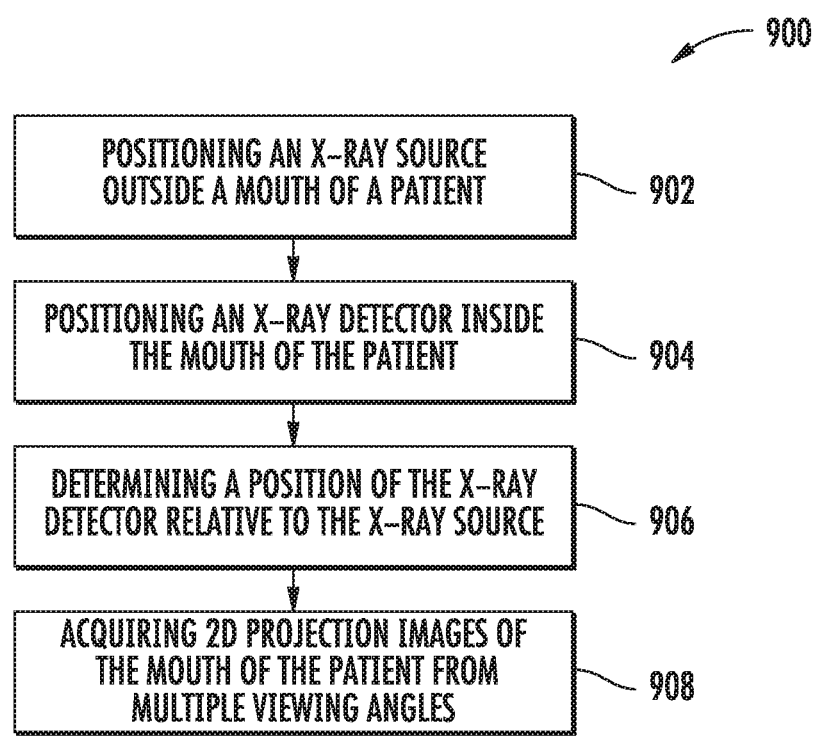
FIG. 9 is a method flow diagram illustrating a method of intraoral three dimensional (3D) imaging using an intraoral tomosynthesis system including a device for determining imaging geometry of the intraoral tomosynthesis system according to some embodiments of the subject matter described herein.

FIG. 9 is a flow diagram depicting an exemplary method, generally designated 900, of intraoral 3D imaging using an intraoral tomosynthesis system including a device for determining imaging geometry of the intraoral tomosynthesis system. The intraoral tomosynthesis system can be, for example system 100, see FIG. 1, while the device for determining imaging geometry can comprise a geometry calibration device, which can be, for example, any of the presently discussed embodiments.

Referring to FIG. 9, in block 902, an x-ray source of the intraoral tomosynthesis system can be positioned outside a mouth of a patient. In some aspects, the x-ray source can contain multiple focal spots spatially distributed on one or multiple anodes in an evacuated chamber. For example, the multiple x-ray focal spots can be spatially distributed along a straight line, a circumference of a polygon, or a 2D pattern in the x-ray source.

In some aspects, the x-ray source can comprise one of a field emission x-ray source array, a thermionic x-ray source array, and a carbon nanotube based field emission x-ray source array.

In block 904, an x-ray detector can be positioned inside the mouth of the patient.

In block 906, a position of the x-ray detector relative to the x-ray source can be determined using the device for determining imaging geometry of the intraoral tomosynthesis system.

In some aspects, the device for determining the imaging geometry of the intraoral tomosynthesis system can comprise a plate connectedly attached to the x-ray detector, at least one light source connectedly attached to the x-ray source, such that the at least one light source is positioned in front of the plate and is configured to project at least one light beam onto the plate, and a camera mounted relative to the at least one light source, the camera being configured to capture at least one light spot produced by a projection of the at least one light beam onto the plate to determine a position of the x-ray detector relative to the x-ray source of the intraoral tomosynthesis system.

In some aspects, the at least one light source can comprise a laser source.

In some aspects, the position of the plate with respect to the x-ray detector can be fixed (e.g., comprise a mechanical linkage) or can be adjustable.

In some aspects, the geometry calibration device can further comprise a gyroscope mounted to the x-ray source for determining an angular position of the x-ray detector relative to the x-ray source.

In block 908, 2D projection images of the mouth of the patient can be acquired from multiple viewing angles by sequentially activating each of the multiple focal spots for a pre-set exposure time, radiation dose, and x-ray energy.

In some aspects, method 900 can further comprise splitting the at least one light beam, using at least one diffraction grating, into multiple light beams each forming a light spot on the plate, such that a light pattern is formed on the plate by at least a portion of the light spots.

In some aspects, method 900 can further comprise positioning the at least one light source such that the at least one light beam projects onto the plate within an enclosed area formed by at least one calibration marker disposed on the plate.

In some aspects, method 900 can further comprise repositioning the plate connectedly attached to the x-ray detector by changing an orientation of the plate and/or changing a translational distance of the plate in an x, y, or z direction relative to the at least one light source.

In some aspects, method 900 can further comprise acquiring a first set of 2D projection images of the mouth of the patient when the plate is in a first position relative to the at least one light source and acquiring a second set of 2D projection images of the mouth of the patient when the plate is repositioned in a second position relative to the at least one light source, the second position being different than the first position.

In some aspects, method 900 can further comprise determining, at at least one computing platform configured to interface with the system in order to determine the position of the x-ray detector relative to the x-ray source of the intraoral tomosynthesis system and/or process the acquired 2D projection images in order to obtain at least one 3D tomography image for display and analysis.

It will be appreciated that exemplary method 900 is for illustrative purposes and that different and/or additional actions may be used. It will also be appreciated that various actions described herein may occur in a different order or sequence.

Although described above with respect to figures for dental imaging, the above systems, methods, and computer readable media can be used for applications other than dental imaging and are not limited to such. Thus, the present subject matter can be embodied in other forms without departure from the spirit and essential characteristics thereof. The embodiments described therefore are to be considered in all respects as illustrative and not restrictive. Although the present subject matter has been described in terms of certain preferred embodiments, other embodiments that are apparent to those of ordinary skill in the art are also within the scope of the present subject matter.

It will be understood that various details of the subject matter described herein may be changed without departing from the scope of the subject matter described herein. Furthermore, the foregoing description is for the purpose of illustration only, and not for the purpose of limitation, as the subject matter described herein is defined by the claims as set forth hereinafter.

What is claimed is:

1. An intraoral tomosynthesis imaging system comprising:
an x-ray source array for positioning outside a mouth of a patient, wherein the x-ray source array contains multiple x-ray focal spots that are spatially distributed on one or multiple anode(s);

an area digital x-ray detector for positioning inside the mouth of the patient;

an x-ray collimator for confining x-ray beams to a region of interest (ROI);

a controller for regulating x-ray radiation and synchronizing the x-ray exposure with the x-ray detector, such that multiple two-dimensional (2D) projection images of the ROI are acquired without moving the x-ray source array, the area digital x-ray detector, or the mouth of the patient; and a computer processor for three-dimensional (3D) tomosynthesis image reconstruction and display.

2. The system of claim 1, further comprising a geometry calibration mechanism to determine the relative position of the x-ray detector placed inside the mouth of the patient with respect to the x-ray source array.

3. The system of claim 2, wherein the geometry calibration mechanism comprises a magnetic attachment attachable to the area digital x-ray detector while inside the mouth of the patient in order to connect the x-ray source array to the area digital x-ray detector.

4. The system of claim 1, wherein the x-ray source array is a field emission x-ray source array.

5. An intraoral three-dimensional (3D) imaging system comprising:

an x-ray source array for positioning outside a mouth of a patient, wherein the x-ray source array contains 3 to 100 x-ray focal spots that are spatially distributed on an anode and spanning an angular range approximately between 3 and 25 degrees, each of the x-ray focal spots being approximately between 0.05 and 2 mm in size;

an area digital x-ray detector for positioning inside the mouth of the patient;

a geometry calibration mechanism connectable to the area digital x-ray detector;

an x-ray collimator for confining x-ray beams to a region of interest (ROI);

an electronic controller for regulating x-ray radiation and synchronization of the x-ray radiation with the area digital x-ray detector, such that multiple two-dimensional (2D) projection images of the ROI are acquired without mechanical motion of the x-ray source array, the area digital x-ray detector, or the mouth of the patient; and a computer processor with executable programs for geometry calibration, tomosynthesis reconstruction, and image display.

6. A method for dual energy intraoral three-dimensional (3D) tomographic imaging, the method comprising:

positioning an area digital x-ray detector at a first position inside the mouth of the patient;

positioning an x-ray source array outside a mouth of a patient, wherein the x-ray source array comprises multiple x-ray focal spots that are spatially distributed on an anode;

acquiring two sets of two-dimensional (2D) projection images of a same region of interest at two different x-ray energies; and processing the two sets of 2D projection images to obtain a reconstructed 3D tomography image with high contrast.

7. The geometry calibration mechanism of claim 2, further configured to provide motion tracking capability during the imaging procedure to dynamically determine the relative position of the x-ray detection with respect to the x-ray source when there is unintentional movement.

8. The geometry calibration device of claim 2, further comprising one or multiple light source(s) mounted on either the x-ray source or the collimator; a screen; a camera; and a mechanism to determine position of the detector with respect to the x-ray source using optical images formed on the screen and captured by the camera.

* * * * *